United States Patent
Cleathero

(10) Patent No.: US 9,687,616 B2
(45) Date of Patent: Jun. 27, 2017

(54) AUTOINJECTOR

(75) Inventor: Ian Charles Cleathero, Leicestershire (GB)

(73) Assignee: The Medical House Limited (GB)

( * ) Notice: Subject to any disclaimer, the term of this patent is extended or adjusted under 35 U.S.C. 154(b) by 439 days.

(21) Appl. No.: 12/988,298

(22) PCT Filed: Apr. 14, 2009

(86) PCT No.: PCT/GB2009/050361
§ 371 (c)(1),
(2), (4) Date: Apr. 7, 2011

(87) PCT Pub. No.: WO2009/127861
PCT Pub. Date: Oct. 22, 2009

(65) Prior Publication Data
US 2011/0178501 A1    Jul. 21, 2011

(30) Foreign Application Priority Data

Apr. 15, 2008   (GB) .................................. 0806814.0
Feb. 6, 2009    (GB) .................................. 0901924.1

(51) Int. Cl.
*A61M 5/32*   (2006.01)
*A61M 5/20*   (2006.01)

(52) U.S. Cl.
CPC .......... *A61M 5/326* (2013.01); *A61M 5/2033* (2013.01); *A61M 5/3257* (2013.01); *A61M 2005/206* (2013.01)

(58) Field of Classification Search
CPC .......... A61M 5/2033; A61M 2005/206; A61M 2005/2073; A61M 5/3202; A61M 5/3257;
(Continued)

(56) References Cited

U.S. PATENT DOCUMENTS 2,309,502 A * 1/1943 Douglas .............. A61M 5/2033
                                                188/67
4,966,592 A * 10/1990 Burns ................. A61M 5/3271
                                                604/198

(Continued)

FOREIGN PATENT DOCUMENTS

FR    2 342 079       9/1977
GB    2452030 A       2/2009
(Continued)

OTHER PUBLICATIONS

International Preliminary Report on Patentability issued by the European Patent Office on Jul. 30, 2010 in connection with related Application No. PCT/GB2009/050361.
(Continued)

*Primary Examiner* — Kevin C Sirmons
*Assistant Examiner* — William Carpenter
(74) *Attorney, Agent, or Firm* — Kolisch Hartwell, P.C.

(57) ABSTRACT

An autoinjector including a housing, in which can be mounted a syringe having a plunger, a barrel and needle at one end thereof through which medicament can be delivered to an injection site; a syringe support means capable of causing said syringe to move therewith along an axial path with respect to said housing; biasing means capable of biasing said syringe support means so that said needle is normally inside said housing, blocking means selectively moveable by a user from a first position in which rearward movement of the syringe along said axial path is substantially prevented, to a second position in which rearward movement of the syringe along said axial path relative to said housing is possible and said biasing means causes said needle to retract inside said housing.

30 Claims, 23 Drawing Sheets

(58) Field of Classification Search
CPC ........ A61M 5/3271; A61M 2005/2013; A61M 5/3287; A61M 2005/3261; A61M 2005/3264; A61M 5/20; A61M 5/3234; A61M 5/326; A61M 2005/3265; A61M 2005/3267; A61M 2005/3263
USPC ......... 604/117, 131–139, 156, 157, 192–198
See application file for complete search history.

(56) References Cited

U.S. PATENT DOCUMENTS

| | | | | |
|---|---|---|---|---|
| 5,411,487 | A * | 5/1995 | Castagna | 604/198 |
| 5,451,210 | A * | 9/1995 | Kramer et al. | 604/137 |
| 6,517,517 | B1 * | 2/2003 | Farrugia et al. | 604/131 |
| 6,613,022 | B1 * | 9/2003 | Doyle | A61M 5/326 |
| | | | | 604/192 |
| 6,979,316 | B1 * | 12/2005 | Rubin et al. | 604/156 |
| 7,645,265 | B2 * | 1/2010 | Stamp | 604/136 |
| 7,670,314 | B2 * | 3/2010 | Wall et al. | 604/135 |
| 7,988,675 | B2 * | 8/2011 | Gillespie et al. | 604/181 |
| 2002/0156426 | A1 * | 10/2002 | Gagnieux | A61M 5/326 |
| | | | | 604/197 |
| 2005/0027255 | A1 * | 2/2005 | Lavi | A61M 5/2033 |
| | | | | 604/135 |
| 2011/0178501 | A1 * | 7/2011 | Cleathero | 604/506 |
| 2011/0282278 | A1 * | 11/2011 | Stamp | A61M 5/2033 |
| | | | | 604/110 |

FOREIGN PATENT DOCUMENTS

| | | |
|---|---|---|
| WO | 9903529 A2 | 1/1999 |
| WO | 9953979 A1 | 10/1999 |
| WO | 03/097133 A1 | 11/2003 |
| WO | 03092771 A1 | 11/2003 |
| WO | 2004060445 A2 | 7/2004 |
| WO | 2004/108194 A1 | 12/2004 |
| WO | 2005/070481 A1 | 8/2005 |
| WO | 2005/079441 A2 | 9/2005 |
| WO | 2005/079441 A3 | 9/2005 |
| WO | 2007/083115 A1 | 7/2007 |
| WO | 2008113198 A1 | 9/2008 |
| WO | 2009/063030 A1 | 5/2009 |

OTHER PUBLICATIONS

U.K. Intellectual Property Office, "Search Report Under Section 17" in connection with related GB Application No. GB0901924.1, dated Mar. 9, 2009, 2 pages.

* cited by examiner

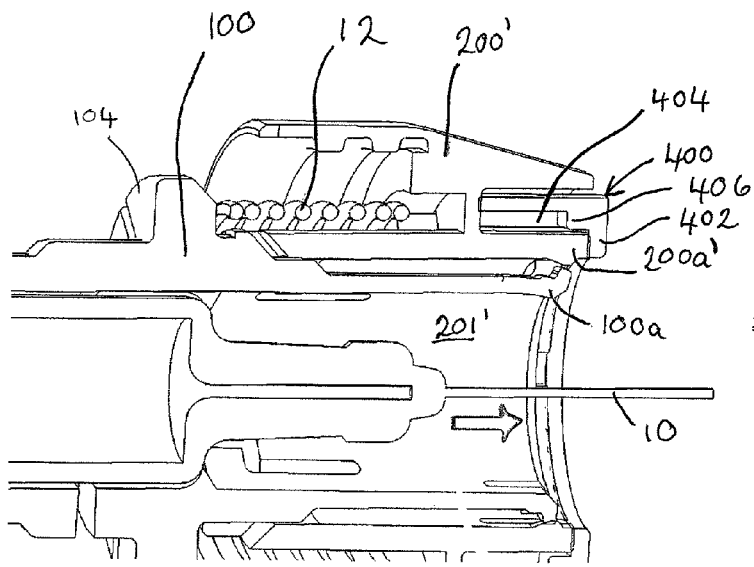
FIGURE 10
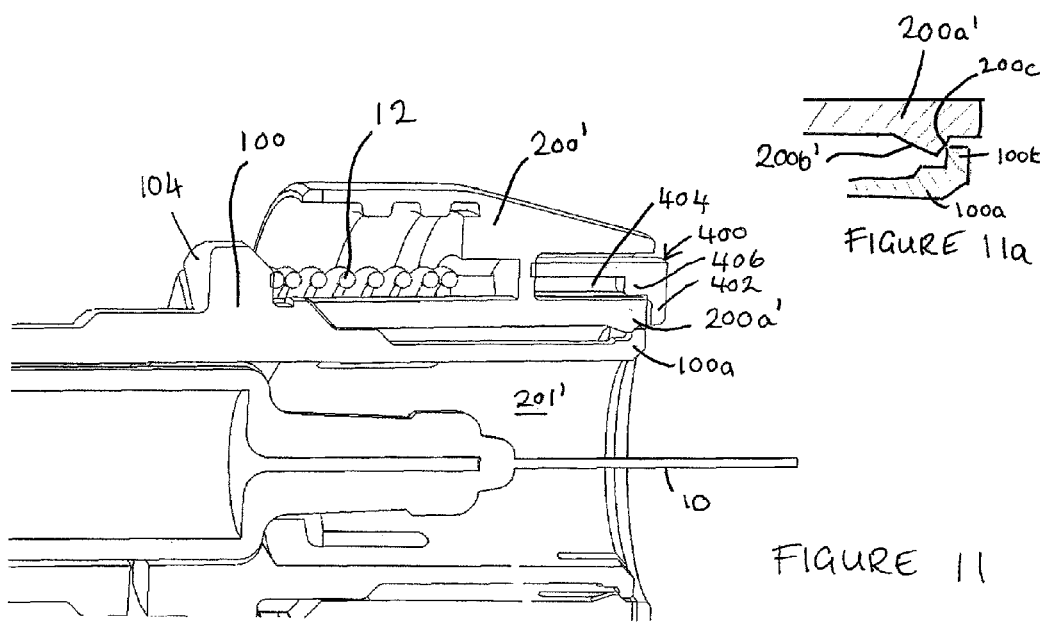
FIGURE 11a
FIGURE 11

AUTOINJECTOR

The present application is the National State Entry under §371 (c) of PCT/GB2009/050361 filed 7 Apr. 2011, and published as WO 2009/127861 on 22 Oct. 2009, which claims foreign priority benefit to GB 0806814.0 filed 15 Apr. 2008 and GB 0901924.1 filed 6 Feb. 2009.

This invention relates to the field of autoinjectors for the administration of liquid medication, for example, interferon.

BACKGROUND

An autoinjector is an automatic injection device designed to facilitate automated delivery of a dose of medicament to a patient through a hypodermic needle, the injection usually being administered by the patient themselves. An autoinjector works, for example, by delivering an injection automatically upon actuation by the patient pressing a button, moving a lever or part of a housing etc. This is in contrast to a conventional manual syringe where the patient himself needs to directly depress a plunger into a barrel containing medicament in order to effect the injection. The terms "autoinjector" and "injection device" are used interchangeably in the following description.

Examples of autoinjectors are described in WO2003/099358 (Seedlings Life Science Ventures LLC) and WO01/93926 (Mayo Foundation for Medical Education and Research). These are both generally flat devices which are of small size to encourage users to carry the device with them for ready access. GB2396298 (PA Consulting Services Ltd) is an example of a more conventionally-shaped elongate autoinjector, but of relatively complex internal construction.

All three of the above prior art devices have a custom designed medicament chamber therein rather than being built around a standard pre-filled syringe presentation. The custom medicament chamber, although allowing for a compact overall size for the device, means that the device as whole must be subjected to more rigorous regulatory control as compared with a device containing a standard pre-filled syringe presentation which will have already obtained regulatory approval.

In general, an autoinjector includes a needle which is located within the housing of the device. Upon activation of a force-generating source, a portion of the needle extends out of the housing and penetrates the outer layer of skin to deliver medicament. In some known autoinjectors, after activation, a needle cover or needle shield moves forward to conceal the needle after use. In GB2396298, the needle automatically retracts back into the housing by means of a biasing spring.

An improved autoinjector is described in our international patent application, published under number WO 2005/070481. Some of the reference numerals in the present application correspond with the equivalent components in the device described in WO 2005/070481. This device requires that the needle is moved axially so that it can appear beyond the end of the nozzle for the duration of the injection, after which the needle retracts automatically, so that it is never in sight of the user. The device also requires that the plunger is moved axially so that medicament is ejected. The overall complexity of the autoinjector is significantly reduced by both of these requirements being effected by one component, namely an inner housing and the device has the significant advantage that it can be built around a conventional or standard syringe presentation.

The injection device of WO 2005/070481 is designed to be used in conjunction with a standard drug presentation e.g. a pre-filled syringe comprising a needle, barrel pre-filled with medicament and a plunger. The plunger may include a separately-provided plunger rod. As mentioned above, there is a significant commercial advantage in being able to use a standard pre-filled syringe, which will have been subjected to numerous clinical trials, drug stability studies and regulatory approval. Any modification to the standard syringe may require further trials and approval, adding delay and expense.

In use, as described in WO 2005/070481, there are three stages of delivering an injection. Before delivering an injection (referring to FIG. 1 of the present application), the end cap 15 is pulled off, removing the needle cover 17 (if present) and rubber needle sheath 16 with it from the needle. In the first stage of delivering an injection, as shown in FIG. 2 of the present application, the tags 7B at the forward end of the inner housing 7 are in contact with the syringe barrel 90, which is pushed axially forward (taking the syringe holder 9 with it), so that the needle 10, which is fixed to the front end of the barrel, moves in the direction indicated by the arrow so that eventually it protrudes beyond the nozzle 11 at the front of the device. Forward travel of the barrel and syringe holder is limited when a surface 9A of the syringe holder reaches an endstop 11A inside the nozzle or front housing 11.

Referring now to FIG. 3, the second stage of the injection is the delivery of the medicament wherein the tags 7A at the rear of the inner housing 7 depress the plunger 8 into the barrel of the syringe in order to deliver medicament to the injection site.

In the third stage of the injection (not illustrated in the present application but shown in WO 2005/070481), once the medicament has been delivered and the inner housing 7 is no longer in contact with the barrel or plunger of the syringe, the secondary spring 12 automatically pushes the syringe holder (and hence the syringe contained therein) axially rearwardly so as to retract the syringe back into the housing so that the used needle is concealed from view.

In our application WO 2007/083115 (see FIG. 5) the syringe holder 9 is replaced by a syringe holder 100 (or "syringe support") that comprises an elongate rear portion 102 a barrel seat 101 (equivalent to barrel seat 91 in FIGS. 1-3) at the rear end of the rear portion 102. The syringe holder also has an intermediate portion 105 of comparable diameter to the rear portion 102, and a front portion 106 of narrower diameter. The intermediate portion 105 is provided with a discontinuous annular flange 104.

WO 2007/083115 discloses a modified front housing 200 (analogous to nozzle 11 in FIGS. 1-3) which is illustrated in FIG. 4. The front housing 200 has a bore 201, of sufficient diameter to allow passage therethrough of the needle, a needle cover and front and intermediate portions of the syringe holder.

The interior surface of the bore 201 is provided with two (or more) equispaced longitudinal slots 202, each having a rear section 203 with a tapered surface providing a varying depth and a forward section 204 of substantially constant depth. The boundary between the forward and rear sections of each slot 202 is defined by a step 205.

The slots 202 provide axial and radial location for the syringe holder 100 as it is inserted therein.

The front housing 200, end cap 300 and syringe holder 100 are supplied in this ready-assembled condition, together with the ready-assembled rear part of the injection device, for final assembly with a pre-filled syringe.

FIG. 6 shows the fully assembled injection device including syringe holder 100. It can be seen that (unlike in the device of FIGS. 1-3) the flange 90 of the barrel does not contact the barrel seat 101 of the syringe holder 100, there being a gap G therebetween. This is a result of the relative axial positions of the syringe holder and syringe being determined at the front end, by gripping means 109 and a front shoulder 92 of the syringe 90.

The devices shown in WO 2005/070481 and WO 2007/083115 automatically retract the needle immediately after dose of the medicament has been delivered. This requires no intervention from the user. However, in some cases, automatic retraction may be undesirable as it could lead to the medicament siphoning back up the needle and out of the patient. In addition, excessively quick retraction of the needle after delivery may cause the medicament to escape from the puncture hole created by the needle in the tissue. This is a known problem when using adrenaline for example.

BRIEF SUMMARY OF THE DISCLOSURE

In accordance with a first aspect of the present invention there is provided an autoinjector including
  a housing, in which can be mounted a syringe having a plunger, a barrel and needle at one end thereof through which medicament can be delivered to an injection site;
  a syringe support or syringe support means capable of causing said syringe to move therewith along an axial path with respect to said housing;
  biaser or biasing means capable of biasing said syringe support means so that said needle is normally inside said housing,
  blocker or blocking means selectively moveable by a user from a first position in which rearward movement of the syringe along said axial path is substantially prevented, to a second position in which rearward movement of the syringe along said axial path relative to said housing is possible and said biasing means causes said needle to retract inside said housing.
Preferably, the housing includes
an outer housing;
an inner housing, at least part of which is positionable, in use, intermediate the outer housing and the syringe support means; and
a rear housing intermediate said outer housing and said inner housing,
the autoinjector further comprising an energy source in communication with said inner housing, the inner housing being moveable by the energy source between three positions, namely
  a first position in which the inner housing is in communication with the barrel such that, in use, the plunger and barrel are movable axially so as to move at least part of said needle out of the outer housing;
  a second position in which the inner housing is in communication with the plunger but not the barrel such that, in use, said plunger is movable axially into said barrel so as to expel medicament through the needle; and
  a third position in which the inner housing is in communication with neither the plunger nor the barrel such that, in use, the plunger and barrel are able to retract in order to retract the needle into the outer housing.
Preferably, said blocking means is selectively moveable by a user from said first position to said second position by the release or reduction of a previously-applied forward force after delivery of a partial, but not necessarily complete, dose of medicament.

In one embodiment, said blocking means comprises a releasable latch between said housing and said syringe support means, preferably including a forward biased locking ring and a needle return spring at a forward end thereof, said locking ring being forward biased by said needle return spring. Said releasable latch is preferably located at a front end of said syringe support means.

In an alternative embodiment, said blocking means comprises a releasable latch between at least part of said inner housing and said rear housing, the releasable latch preferably comprising a radially-flexible tag on said inner housing which is capable of moving into and out of engagement with an aperture or recess in said rear housing. Preferably the autoinjector further comprises rearward biasing means between said outer housing and said rear housing, for example a spring beam or a spring intermediate a rear end of said rear housing and said outer housing.

In a further alternative embodiment, said blocking means comprises a releasable latch between at least part of said outer housing and said rear housing, the releasable latch preferably comprising a longitudinal slot in one of said outer housing and rear housing, into which a rib or protrusion on the other of said outer housing and rear housing can engage. Preferably, said longitudinal slot has a main section of substantially constant width and a forwardmost section of narrowed width with a tapered edge therebetween, wherein, in use, forward movement of said rib or protrusion in said slot is guided by said tapered edge so as to cause rotary movement of said rib or protrusion about the longitudinal axis of the autoinjector. Preferably, said longitudinal slot is in said rear housing and said a rib or protrusion is on the interior surface of said outer housing.

According to a second aspect of the invention there is provided a method of delivering medicament using an autoinjector as claimed in any of the preceding claims comprising the steps of:
  placing the forward end of the autoinjector at an injection site;
  applying a forward force to the autoinjector which a) engages said blocking means into said first position and b) initiates delivery of medicament;
  releasing said forward force at a time selected by the user which a) causes said blocking means to move into said second position and b) permits retraction of said needle into said housing.

BRIEF DESCRIPTION OF THE DRAWINGS

Preferred embodiments of the present invention will now be more particularly described, by way of example only, with reference to the accompanying drawings in which:

FIG. 10 is a cross sectional side view of the device of FIG. 7 as it appears as the syringe holder is moving forward prior to delivery of medicament;

FIG. 11 is a cross sectional side view of the device of FIG. 7 as it appears during delivery of the medicament;

FIG. 11a is a detailed view of a front housing flexible arm engaging with an syringe holder flexible arm as shown in FIG. 11;

FIG. 23b is a cross section of the device of FIG. 23a and FIG. 23c is a detailed view of the inner housing rear legs of the device of FIG. 23a;

DETAILED DESCRIPTION

Figure 1:
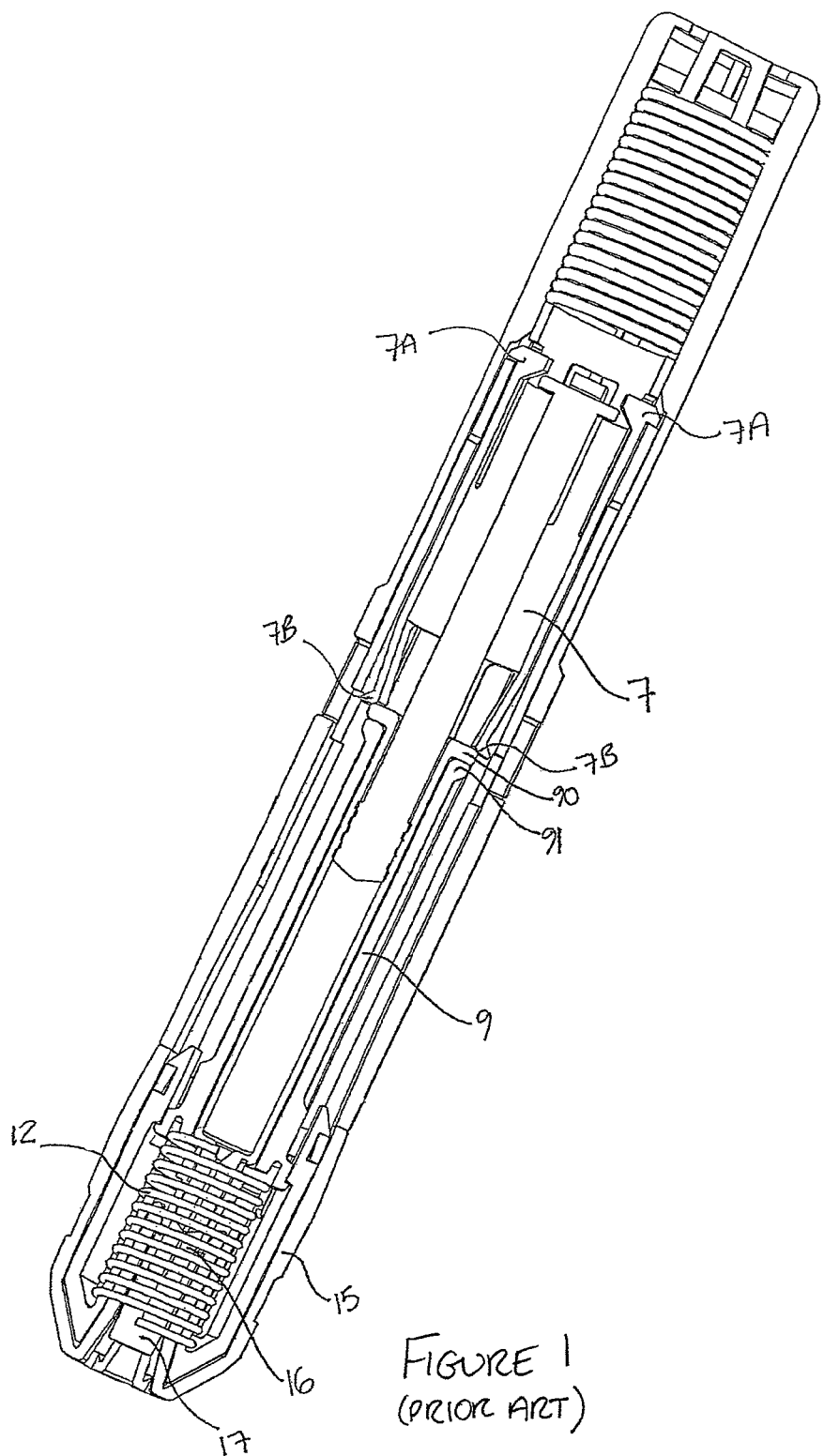
FIG. 1 (PRIOR ART) is a perspective view of a known injection device.

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Throughout the following description, reference to a "forward" direction means the direction which is towards the patient when the injection device is in use. The "forward" end of the injection device is the end nearest the patient's skin when the device is in use. Similarly, reference to a "rearward" direction means the direction which is away from the patient and the "rearward" end of the device is the end furthest from the patient's skin when the injection device is in use.

The "plunger" includes any elastomeric stopper or the like which seals the chamber containing liquid medicament. The plunger typically also includes a plunger rod but this may be provided separately from the elastomeric stopper and need not be an essential part of the syringe. The "forwardmost position" of the plunger refers to the forwardmost position of any part of the plunger (typically the forwardmost edge of the stopper).

Features, integers, characteristics or groups described in conjunction with a particular aspect, embodiment or example of the invention are to be understood to be applicable to any other aspect, embodiment or example described herein unless incompatible therewith.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

As described above, in prior art devices, retraction of the needle occurs automatically after the dose of medicament has been delivered regardless of whether the user wishes it to do so or not. In some situations, it may be preferable for the user to have control over the timing of the needle retraction. In general, the dwell time of the needle within the tissue needs to be sufficiently long for the entire medicament to be delivered so that it does not siphon back up through the needle or escape through the puncture hole in the tissue as the needle is withdrawn. The dwell time for a particular medicament is dependent on many factors including its viscosity and the nature of the tissue into which it is to be delivered. As such, it is desirable that the user administering the medicament has control over the length of time that the needle remains in the tissue after the medicament has been delivered. The present invention provides the user with this control.

Figure 4:
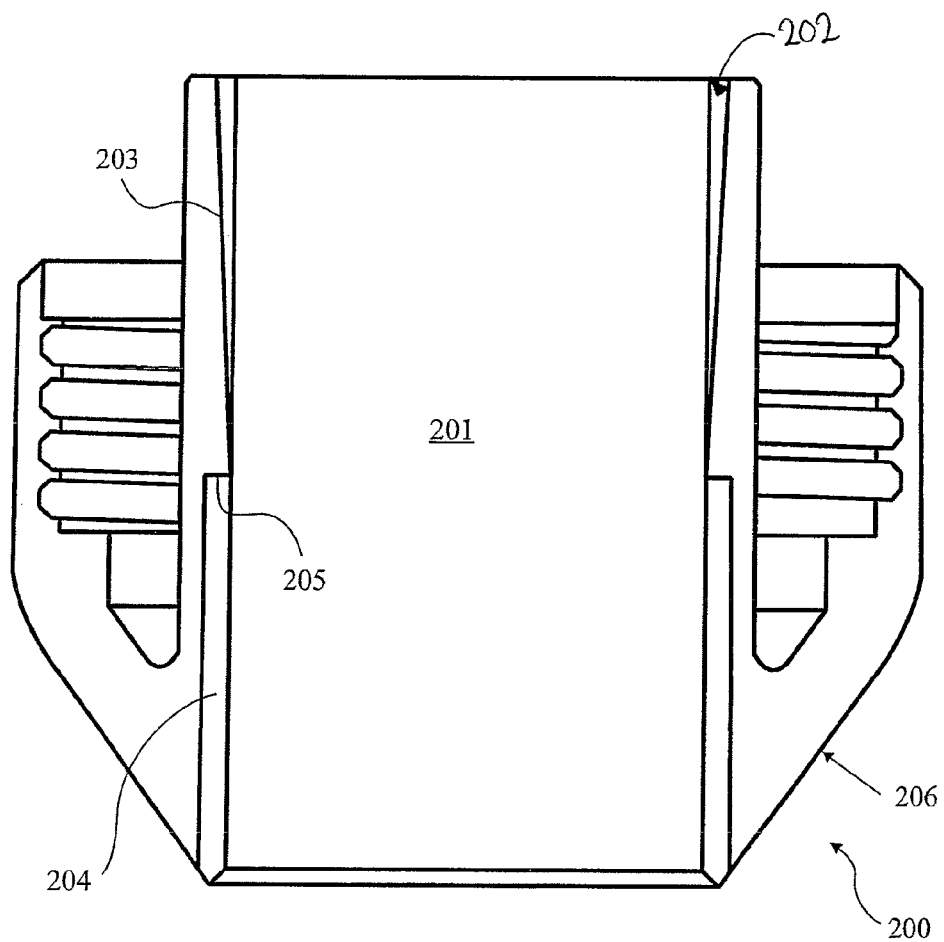
FIG. 4 (PRIOR ART), drawn to a larger scale, is a cross-sectional view of the modified front housing.
Figure 5:
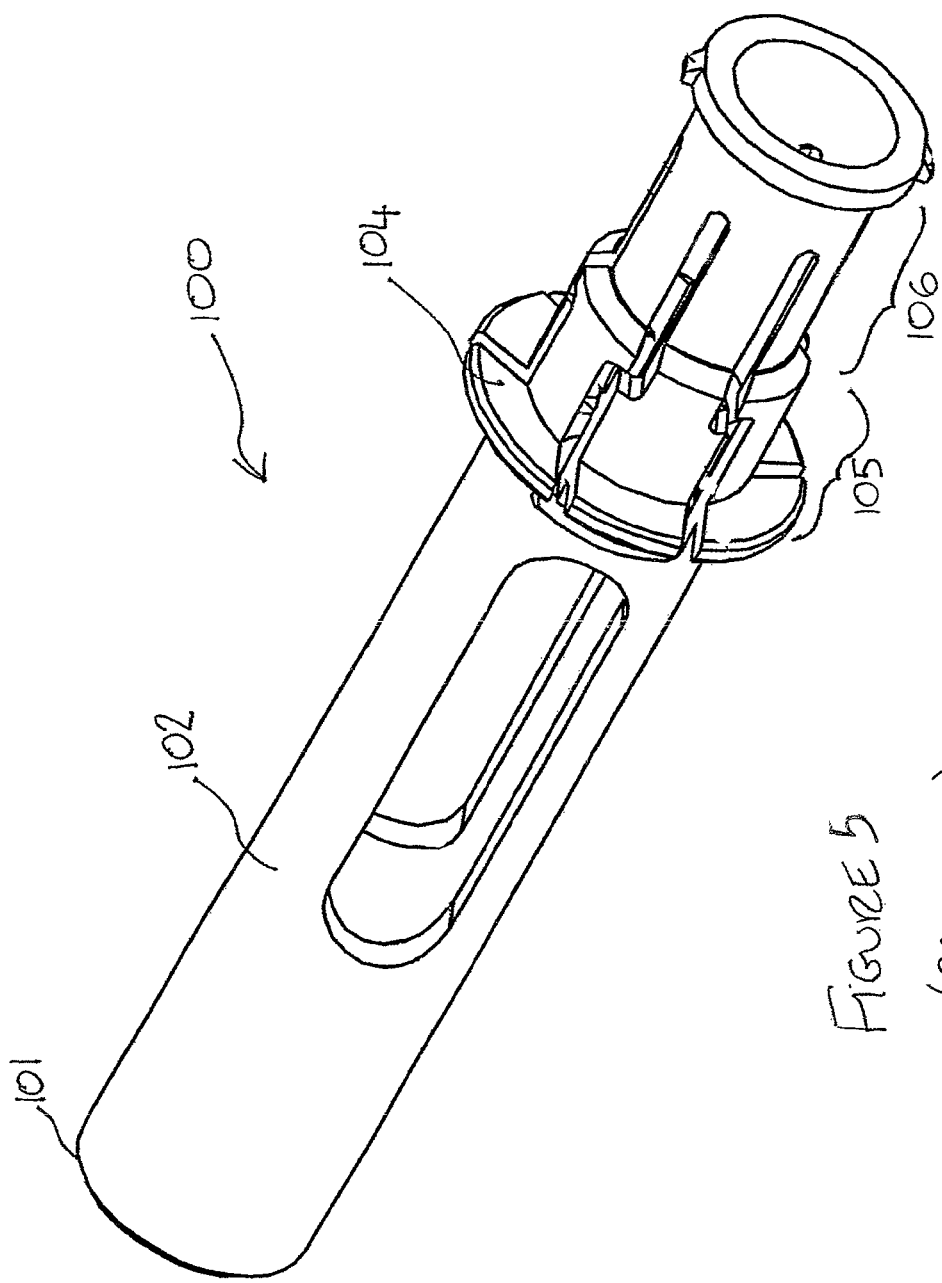
FIG. 5 (PRIOR ART) is a perspective view of a syringe holder.
Figure 6:
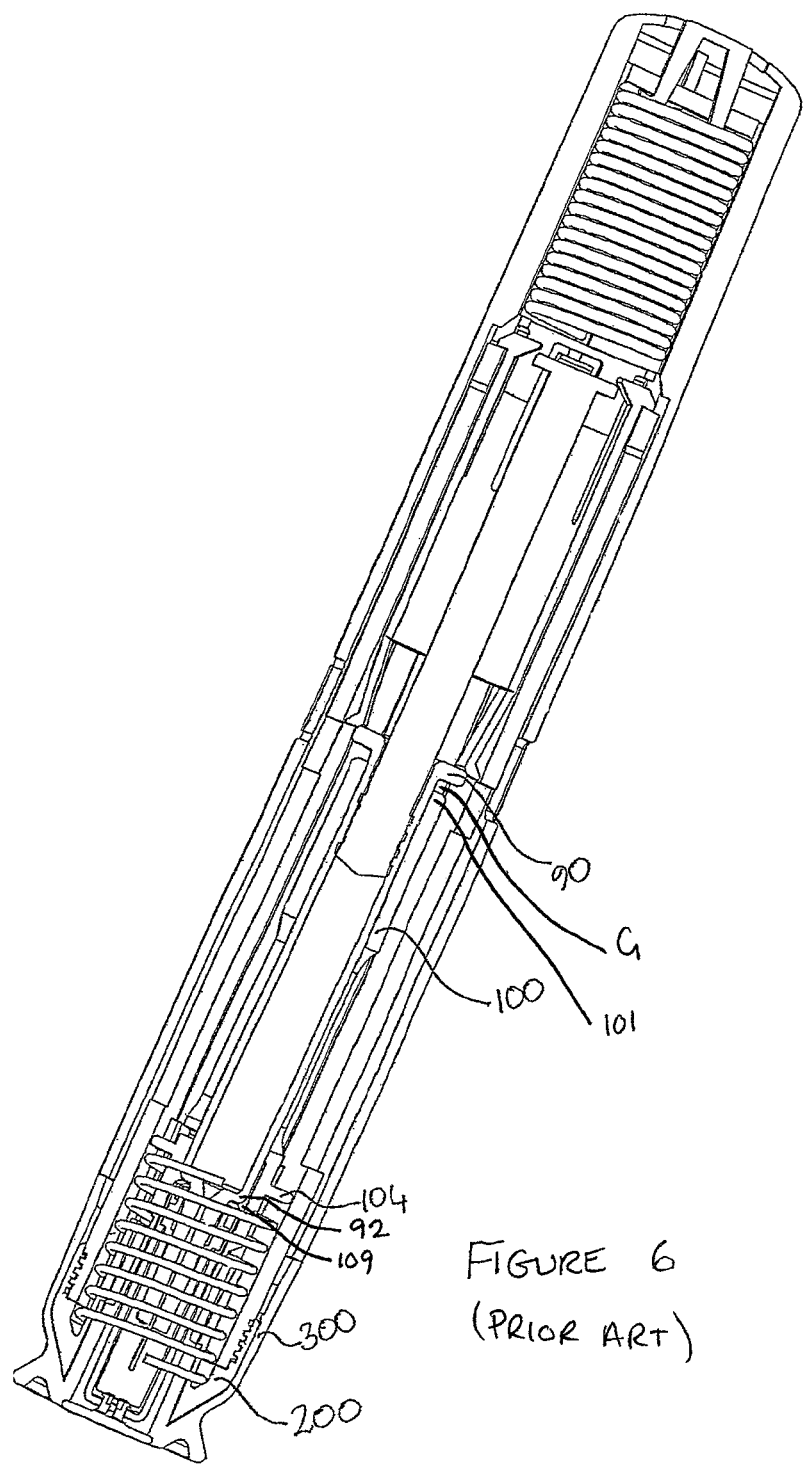
FIG. 6 (PRIOR ART) is a perspective view of an assembled injection device.
Figure 7:
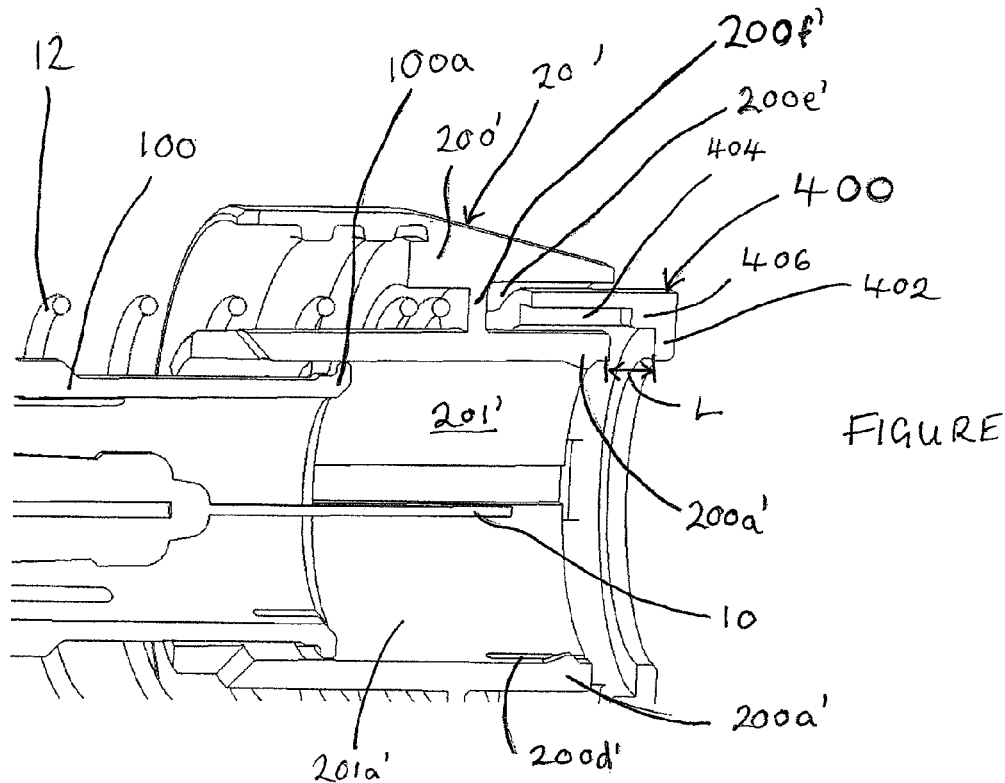
FIG. 7 is a cross-sectional side view of an injection device comprising a modified front housing and a retraction ring prior to use.

As shown in FIG. 7, a modified front housing 200' (analogous to front housing 200 in the prior art) is provided with a retraction ring 400 (or "locking ring"). The front housing 200' has a bore 201', of sufficient diameter to allow passage therethrough of the needle 10, needle cover (not illustrated) and front and intermediate portions of the syringe holder 100 (but not the flange 104 (see FIG. 10)). The bore 201' is surrounded by an interior surface 201a' of the front housing 200'. The front housing 200' differs from the prior art (FIG. 4 for example) in that it includes flexible arms 200a' defined by radially spaced slots 200d' in the interior surface 201a' surrounding the bore 201'. The flexible arms 200a' thus form part of the interior surface 201a' which surrounds the bore 201'. The flexible arms 200a' are each provided with a first, rearmost, ramp 200b' and a second, forwardmost, ramp 200c' on their interior surface (see FIG. 11a). The first and second ramps 200b', 200c' rise towards one another to meet at a point. The gradient of the first ramp 200b' is preferably less than the gradient of the second ramp 200c'.

At the forwardmost end of the front housing 200', there is provided an axially-extending annular slot 200e'. The slot 200e' is open at its forwardmost end and closed by a partition 200f' at its rear end. The partition 200f' forms a discontinuous annular flange around the outside of the interior surface 201a' and connects to an outer portion 202' of the front housing 200'. The retraction ring 400 is received in the slot 200e'.

Figure 9:
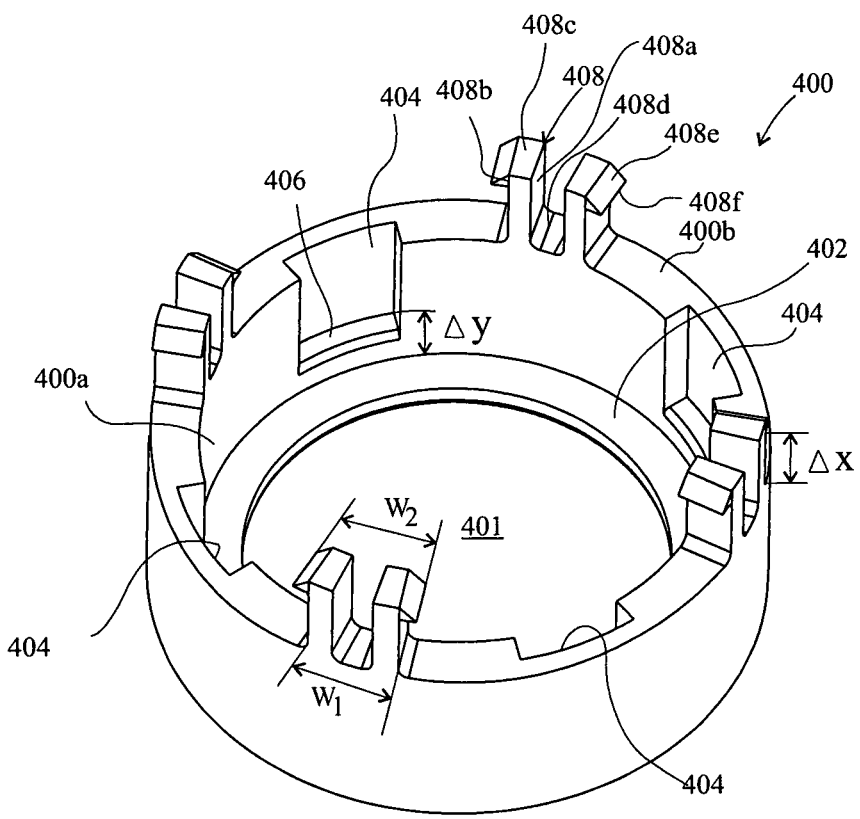
FIG. 9 is a detailed perspective view of the retraction ring.

The retraction ring 400 is shown in detail in FIG. 9, where it can be seen that it is generally cylindrical in shape having a bore 401. The retraction ring has a main body 400a, rim 402 and rear legs 408. The rim 402 defines a front annulus where the inner diameter of the rim 402 is less than the inner diameter of the main body 400a. The interior surface of the main body 400a is provided with recesses 404 which extend from a rear end 400b of the ring 400 and terminate intermediate the rear end 400b and rim 402. The forwardmost portions of the recesses 404 are defined by steps 406 whose size Δy is equal to the distance between the forwardmost portion of a recess 404 and the rim 402.

Projecting rearward from the rear end 400b are several pairs of flexible legs 408 positioned along the circumference of the retraction ring 400. For each pair, a gap 408d separates the legs 408 defining a space into which the legs 408 can flex. The legs 408 have a first leg section 408a extending rearward and a second leg section 408b projecting substantially perpendicular the first leg section 408a in a direction away from the gap 408d. The second leg section 408b is wedge shaped with a tapered leading surface 408e on a rear side and a substantially flat surface 408f that is substantially perpendicular the first leg section 408a on a front side. In one embodiment, the rearmost portion 408c of the first leg section 408a is a substantially flat plane that is substantially perpendicular to the first leg section 408a. The first leg sections of a pair define a width $W_1$, whilst the second leg sections of a pair define a width $W_2$.

When the retraction ring is assembled in the autoinjector during assembly, the legs 408 of retraction ring 400 pass through apertures 410 (see FIG. 8) within the partition 200f'. To do this, the legs 408 must flex inward into the gap 408d such that the second leg sections 408b can pass through the apertures 410 i.e. such that $W_2 \leq W_1$ (in a flexed state). For a good fit, it is preferable that the apertures 410 have a similar size $W_A$ (not indicated on Figures) to that $W_1$ defined by the first leg sections 408a of each pair. However, for reasons that are explained below, the aperture 410 width should be slightly wider than $W_1$ but less than $W_2$ (in a relaxed state). As the retraction ring 400 is pushed into the slot 200e' of the front housing 200', the tapered surfaces 408e contact the edges defining the apertures 410 and are urged in toward the gaps 408d, the first leg sections 408a flexing as they do so. The first leg sections 408a spring back to their original relaxed position once the second leg sections 408b pass through the apertures 410. At this point $W_2 > W_1$ once again, and $W_2 > W_A$ also. The retraction ring 400 is then secured to the front housing 200' since abutment between the flat surfaces 108f and the edges defining the apertures 410 prevent any axial force being translated into forces capable of flexing the legs 408.

When installed onto the front housing 200', the rear portions 408c of the legs contact the secondary spring or return spring 12 that is used to retract the needle after delivery of medicament. Provided that $W_2 > W_A > W_1$, the retraction ring has an axial degree of freedom such that the legs 408 can move axially within the apertures 410 by an amount Δx defined by the distance between the rear end 400b of the retraction ring 400 and the flat surfaces 408f of the legs 408. In practice however, the retraction ring 400 is urged forward by the secondary spring 12 such that a rearward external force is required to move the retraction ring 400 rearward. FIG. 7 shows the retraction ring 400 installed onto the front housing 200' where the retraction ring 400 is urged forward by the secondary spring 12.

To administer the medicament to the patient, the device must first be applied to the injection site, for example the patient's thigh. To do this the user pushes the front end of the device against the tissue into which the medicament is to be delivered. The forward force on the device causes the retraction ring 400 to move rearward (indicated by arrow on FIG. 8) with respect to the front housing 200' acting against the forward biasing force of the secondary spring 12. The retraction ring 400 can move rearward relative the front housing until the flexible arms 200a' of the front housing 200' abut the rim 402 of the retraction ring 400. It is therefore preferable that the distance L (indicated on FIG. 7) between the flexible arms 200a' and the rim 402 be equal to the amount of travel Δx allowed by the legs 408 such that the abutment of the flat surfaces 108f with the edges defining the apertures 410 and the abutment of the arms 200a' with the rim 402 occurs simultaneously.

Figure 8:
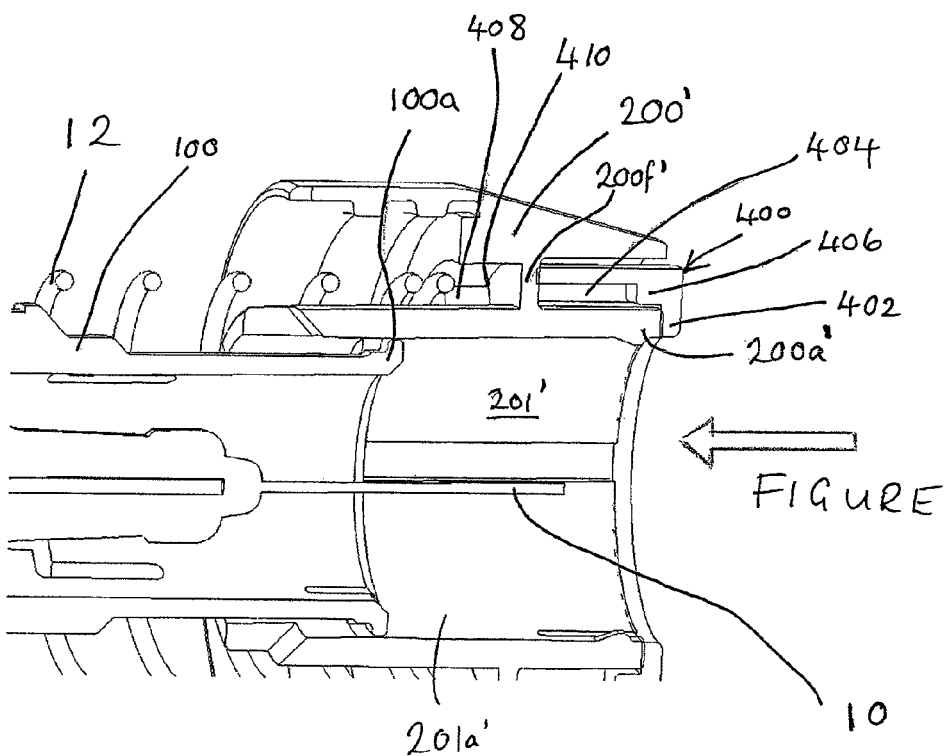
FIG. 8 is a cross sectional side view of the device of FIG. 7 as it appears when applied to an injection site.

With the autoinjector pressed to the injection site and in the position shown in FIG. 8, the arms 200a' are radially restrained through contact with the steps 406 and are thus prevented from flexing radially outward. At this point the device is ready to be actuated deliver medicament. During actuation, the syringe holder 100 moves axially forward under the influence of an energy source compressing secondary spring 12 such that the needle projects out of the bore 201' to penetrate the patient's tissue.

Flexible arms 100*a* are provided at the foremost portion of the syringe holder 100. The flexible arms 100*a* extend axially along the body of the syringe holder and have latches 100*b* extending radially outwards at a forward most end. As the syringe holder 100 moves forward during actuation (indicated by arrow in FIG. 10), the flexible arms 100*a* of the syringe holder 100 contact the ramps 200*b'*, 200*c'* on the front housing flexible arms 200*a'*. More precisely, the latches 100*b* contact the first ramps 200*b'* and are urged radially inwards by contact forces therebetween. FIG. 10 shows the syringe holder flexible arm 100*a* flexed radially inwards through contact with the first ramp 200*b'*. Further forward axial movement of the syringe holder 100 causes the latch 100*b* to pass the peak of the first ramp 200*b'* such that the latch 100*b* slides along the gradient of the second ramp 200*c'*. In doing so, the syringe holder flexible arm 100*a* returns to a relaxed state as shown in FIG. 11. After this point the medicament is delivered, during which time the syringe holder 100 is inhibited from moving axially rearward due to abutment between the latch 100*b* and the second ramp 100*a* (see also FIG. 11*a*).

Return spring 12 acts as a biaser and provides the rearward axial force required for needle retraction. In the position shown in FIG. 11, the return spring 12 is under compression and is exerting a rearward force on the flange 104 of the syringe holder 100 and a forward force on the retraction ring 400 via legs 408. In prior art devices, it is the rearward and forward forces exerted by the return spring 12 that cause the syringe holder (and hence needle) to retract automatically after the medicament has been delivered. However, in the present device, in the position shown in FIG. 11, the front housing flexible arm 200*a'* is restrained from flexing radially outwards by abutment with the step 406. The return spring 12 cannot urge the syringe holder 100 rearwardly because of abutment between the latch 100*b* and the second ramp 200*c'* which acts (with the retraction ring) as a blocker.

Rearward movement of the syringe holder 100 could only occur if a significant axial rearward force was applied to the syringe holder 100 such that the latch 100*b* was urged over the steep gradient of the second ramp 200*c'*. A suitably large axial rearward force cannot be provided by the return spring 12 per se and so needle retraction is prevented when the device is in the state depicted in FIG. 11.

Once the delivery of medicament is complete, the user chooses when to remove the device from the injection site. The user may wish to leave the device in place for a few seconds, depending upon the desired dwell time for the needle delivery of a particular medicament.

In the desired embodiment, user-selected removal of the device from the injection site initiates retraction of the needle at a desired time (as will be explained below). Other embodiments are envisaged wherein, for example, retraction of the needle is initiated by the user pressing a button or otherwise manipulating part of the device.

Figure 12:
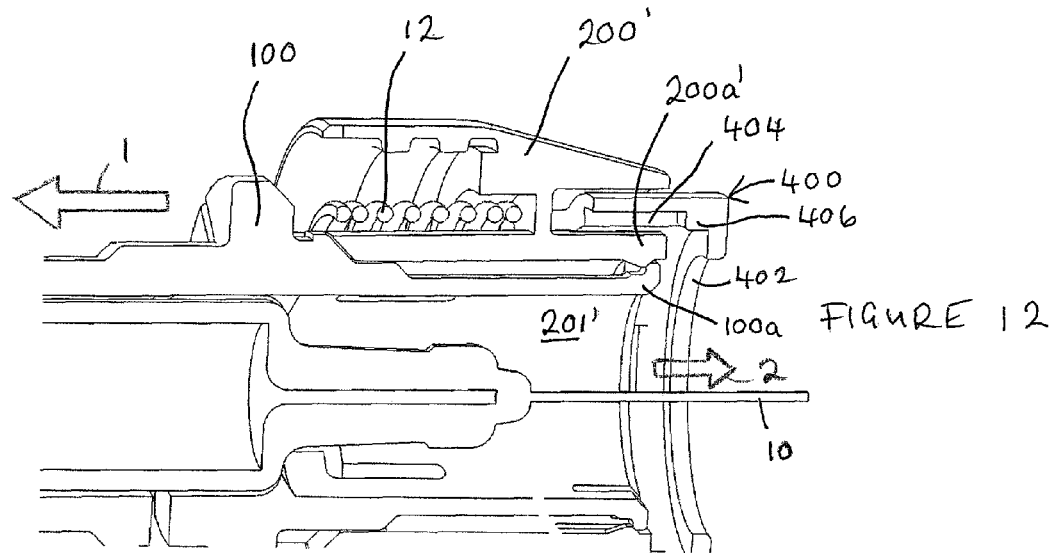
FIG. 12 is a cross sectional side view of the device of FIG. 7 as it appears as the device is removed from the injection site after delivery of the medicament.

The device is removed by applying a rearward force (arrow 1, FIG. 12) to the device. A consequence of removing the device from the injection site is that the rearward axial force applied to the retraction ring 400 by the patient's tissue is also removed. With no external force overcoming the biasing force of the return spring 12, the retraction ring 400 is urged forward (arrow 2, FIG. 12) by the return spring 12. The distance that the retraction ring will move is determined by the distance $\Delta x$.

As soon as the retraction ring 400 moves forward by a distance $\Delta y$ the front housing flexible arm 200*a'* is no longer radially constrained by abutment with the step 406 since the two are no longer radially aligned. The distance $\Delta y$ is defined in FIG. 9 as the axial length of the step 406 (see also FIG. 12). In practice, the length of the step $\Delta y$ should be less than the length L defined in FIG. 7 so that when the retraction ring 400 has moved forward relative the front housing 200', the front housing flexible arm 200*a'* is in radial alignment with the recess 404.

Figure 13:
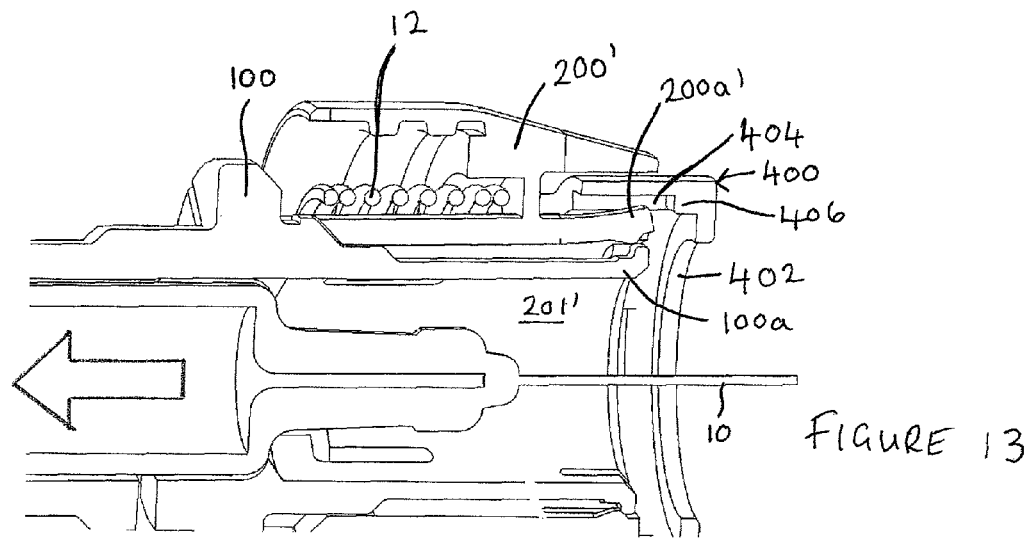
FIG. 13 is a cross sectional side view of the device of FIG. 7 as it appears during needle retraction.
Figure 14:
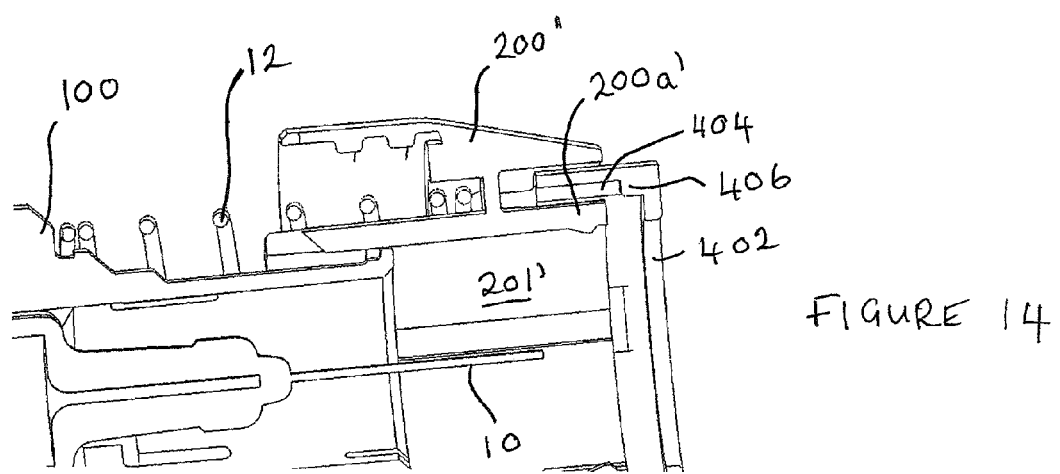
FIG. 14 is a cross sectional side view of the device of FIG. 7 with the needle fully retracted.

It should be noted that the syringe holder flexible arm 100*a* is stiffer than the front housing flexible arm 200*a'* such that the syringe holder flexible arm 100*a* is more resistant to radial movement. As the return spring 12 acts rearwardly on the syringe holder 100, the contact forces between the syringe holder flexible arm 100*a* and the second ramp 200*c'* of the front housing flexible arm 200*a'* cause the weaker front housing flexible arm 200*a'* to flex radially outwards into the recess 404 (FIG. 13). As the front housing flexible arm 200*a'* flexes radially outwards, the ramps 200*b'*, 200*c'* flex out of the axial path of the latch 100*b* such that the syringe holder flexible arm 100*a* has a clear axial path. With no obstructions along the axial path of the syringe holder flexible arm 100*a*, the syringe holder 100 is free to move axially rearward, biased by the return spring 12. As the syringe holder 100 moves rearward (indicated by arrow in FIG. 13), so too does the needle 10 so that the needle retracts into the housing. FIG. 14 shows the device in a relaxed state after medicament has been delivered and needle retraction has taken place.

An advantage of the arrangement described above is that the user initiates needle retraction and can therefore increase the dwell time of the needle for as long as is required or desired. As described above, removal of the device from the injection site causes the retraction ring 400 to move axially forward with respect to the front housing 200'. Relative forward movement of the retraction ring 400 presents a recess 404, in axial alignment, to the front housing flexible arm 404, thus providing space for the flexible arm 404 to flex into and out of the axial path of the syringe holder flexible arm 100*a*. The syringe holder 100 (and therefore needle 10) is then free to retract, urged by return spring 12.

A key component in determining the delay between removal of the device from the injection site and initiation of automatic needle retraction is the step 406 of the retraction ring 400. The size $\Delta y$ of the step 406 is determinative of the distance that the retraction ring 400 must move forward relative the front housing 200' to initiate automatic retraction.

The skilled reader will appreciate that the device need not necessarily be fully removed from the injection site for the retraction ring 400 to move relative the front housing 200'. Rather, the user must reduce the forward force on the device such that the return spring 12 is able to urge the retraction ring 400 forward relative the front housing 200'. It is therefore possible for automatic retraction to initiate whilst the rim 402 of the retraction ring 400 is still in contact with the injection site. The retraction ring 400 would then act as a shroud preventing the user from seeing the needle before automatic retraction is initiated. In the preferable case where the retraction ring 400 maintains contact with the injection site until the needle is fully retracted, the initial withdrawal of the needle from the tissue is consequential of the retraction ring 400 moving forward relative the front housing 200', which is brought about by a reduction in forward pressure on the device. Once the retraction ring 400 has moved a distance Δy relative the front housing 200', automatic retraction of the needle 10 initiates causing complete withdrawal of the needle 10 from the tissue. Therefore, the distance Δy is also determinative of the length of needle 10 that needs to be manually withdrawn from the tissue before automatic (spring biased) retraction takes over. Clearly, the user can take however long he wishes to withdraw the needle 10 by an amount Δy and can therefore delay the onset of automatic needle retraction until desired.

Figure 2:
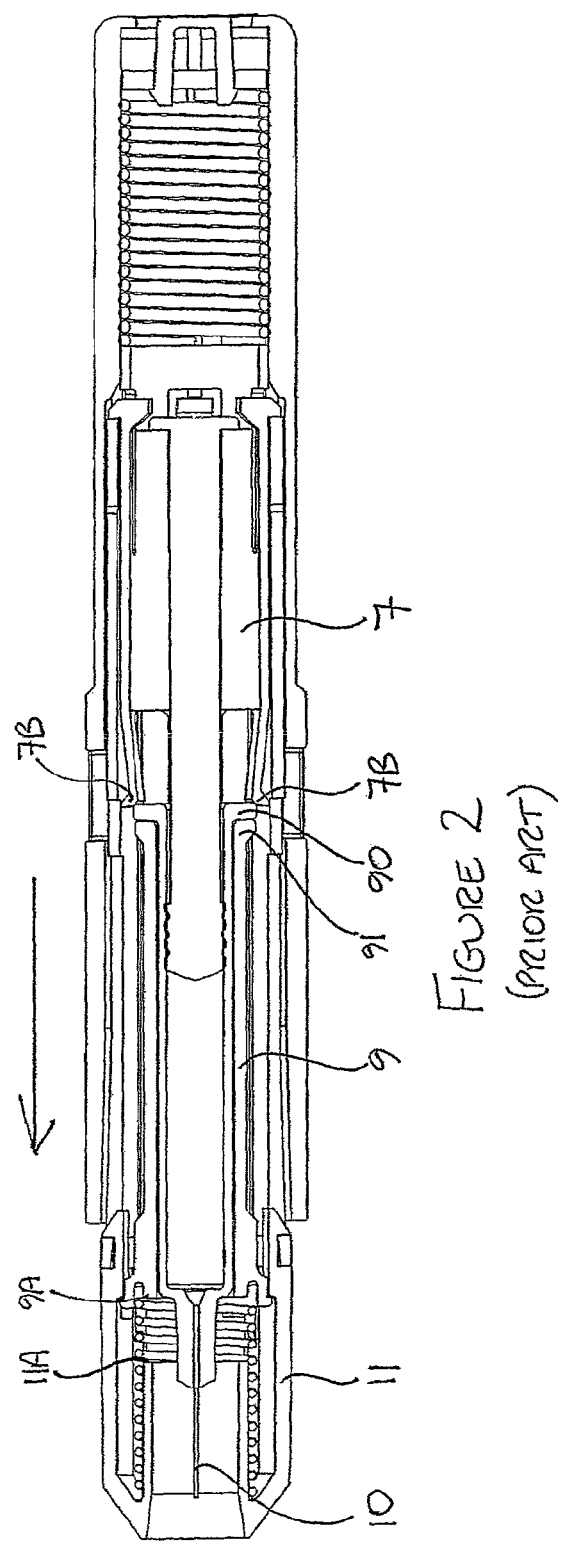
FIG. 2 (PRIOR ART) is a plan view, partly in section of the FIG. 1 device, with the cap and needle cover removed, ready for actuation.
Figure 3:
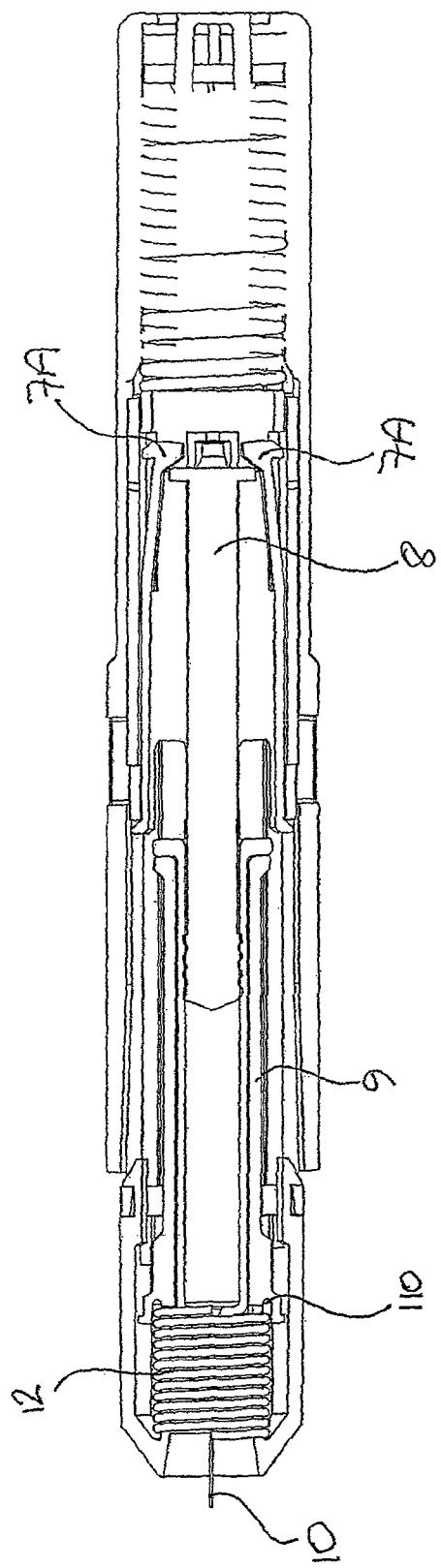
FIG. 3 (PRIOR ART) is a plan view, partly in section of the FIG. 1 device, with the needle exposed, ready for the plunger to be depressed in order to deliver the medicament.
Figure 15:
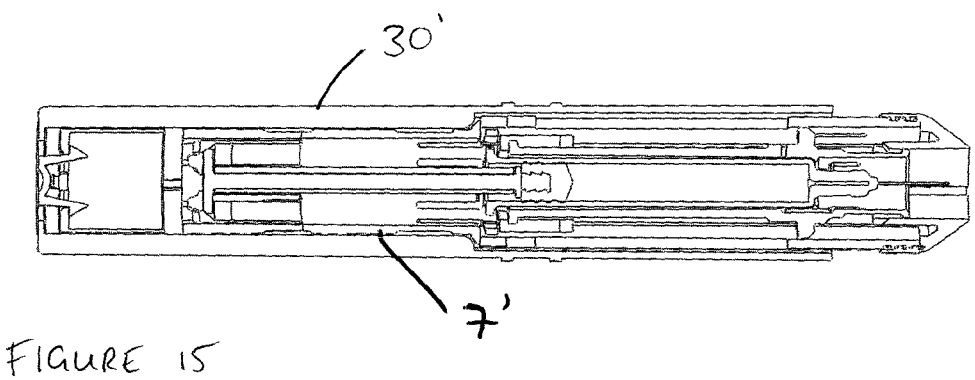
FIG. 15 is a cross sectional side view of an injection device comprising a modified outer housing and a modified inner housing prior to use.

In an alternative embodiment of the device, the retraction of the needle is controlled without utilising a modified front housing or retraction ring. FIG. 15 shows a modified version of the device of FIGS. 1-3, prior to actuation, which includes a modified inner housing 7' and a modified outer housing 30'.

Figure 16:
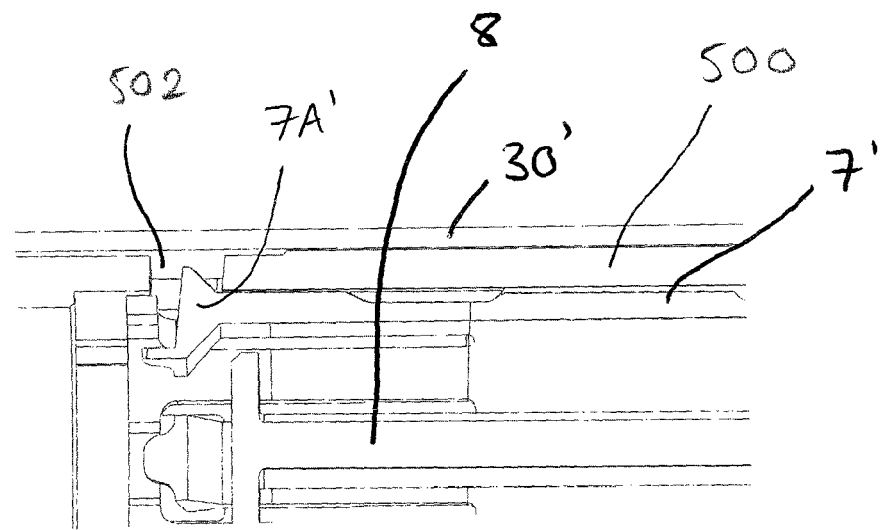
FIG. 16 is a partial cross sectional side view of the device of FIG. 15 showing rear legs of the inner housing disposed in apertures of a rear cylinder prior to use.
Figure 19:
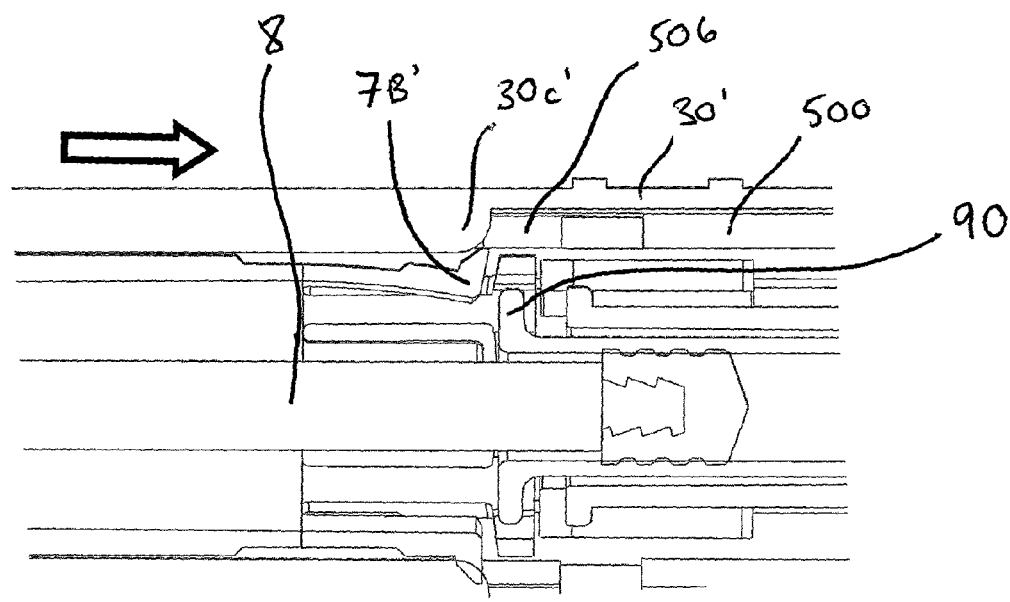
FIG. 19 is a partial cross sectional side view of the device of FIG. 15 showing front legs of the inner housing after the outer housing has been moved forward relative the rear cylinder.

The inner housing 7' is injection moulded as a single piece having, preferably, four orthogonally placed tags at each end thereof. The rear tags 7A' are shown in FIG. 16 and the front tags 7B' are shown in FIG. 19. Each tag 7A', 7B' is at the end of a resiliently flexible leg, cut out of the material of the housing 7', so that each leg (and its respective tag) is able to flex radially with respect to the remainder of the housing 7'.

Figure 17:
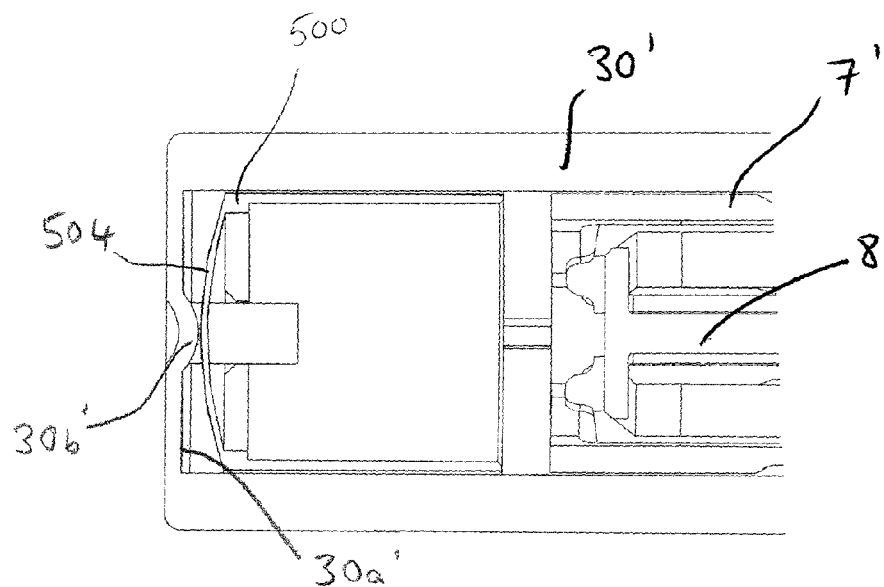
FIG. 17 is a partial cross sectional side view of the device of FIG. 15 showing a spring beam attached to a rear end of the rear cylinder prior to use.

Intermediate the inner housing 7' and outer housing 30' is a rear cylinder 500 (FIG. 16). Prior to actuation, the rear tags 7A' of the inner housing 7' locate in apertures 502 in the rear cylinder. As shown in FIG. 17, a rear end of the rear cylinder 500 or "rear housing" has a flexible spring beam 504 traversing the diameter thereof. The skilled reader will appreciate that other equivalent embodiments may include other elastic elements (a spring, for example) in place of a spring beam.

The inner surface of the rear end 30a' of the outer housing 30' has a protrusion 30b' extending axially forward. Prior to actuation the spring beam 504 is in a relaxed state (as shown in FIG. 17) such that there is substantially no contact force between the protrusion 30b' and the spring beam 504.

Figure 18:
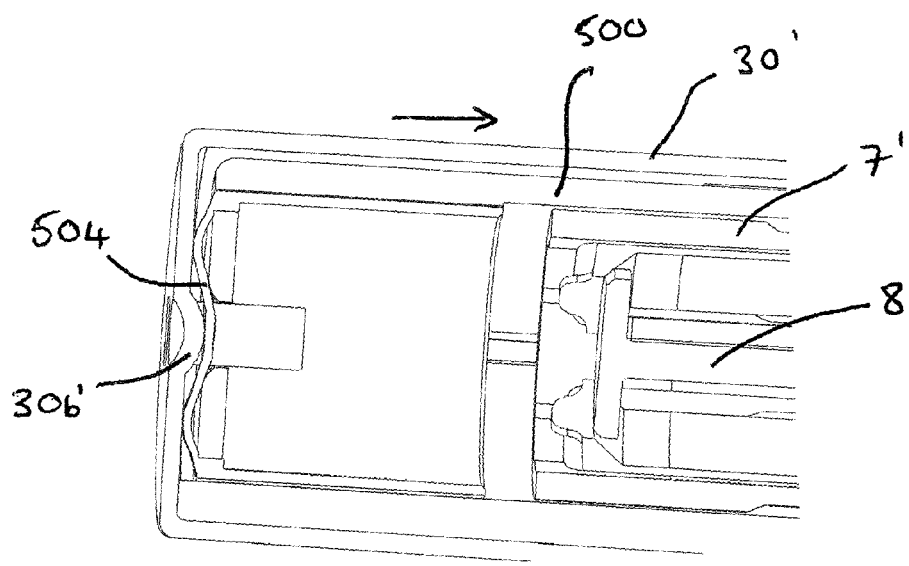
FIG. 18 is a partial cross sectional side view of the device of FIG. 15 after the outer housing has been moved forward relative the rear cylinder.

To use the autoinjector, the user places the front end of the device to an injection site and applies a forward force on the outer housing 30'. The forward force causes the outer housing 30' to move forward relative the inner housing 7' and rear cylinder 500 (as indicated by the arrow in FIG. 18). As the outer housing 30' moves forward, abutment between the protrusion 30b' and spring beam 504 causes the spring beam 504 to compress (as shown in FIG. 18). The outer housing 30' is then subjected to a rearward biasing force from the spring beam 504.

Simultaneously, as the outer housing 30' moves forward so too does an axially extended rib 30c' disposed within the outer housing 30'. As shown in FIG. 19, the advancing rib 30c' contacts chamfered edges of the front tags 7B' causing them to flex radially inwards out of apertures 506 of the rear cylinder 500 in which they were previously located. Once flexed inwards, the front tags 7B' are at least partially in axial alignment with the finger flange 90 of the syringe. The device is now ready to deliver an injection.

Figure 20:
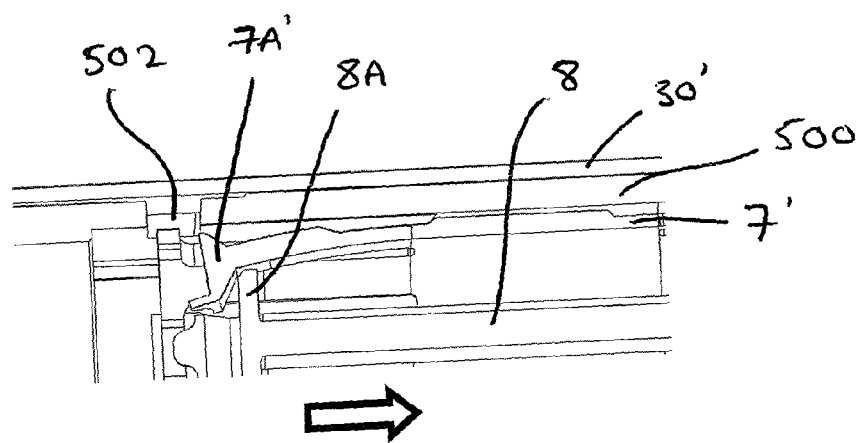
FIG. 20 is a partial cross sectional side view of the device of FIG. 15 showing the inner housing driving a plunger axially forward.

When actuated, the inner housing 7' is driven forward by an enemy source. As the inner housing 7' advances forward, the rear tags 7A' are drawn radially inwards, out from apertures 502, 35 by abutment between a chamfered front side of the rear tags 7A' and the edges defining the apertures 502. When the inner housing 7' advances to the point shown in FIG. 20, the rear tags 7A' are constrained radially between the rear cylinder 500 and a flange 8A of a syringe plunger 8. Further advancement of the inner housing 7' in the direction indicated by the arrow in FIG. 20, relative the outer housing 30', then causes the collective forward axial movement of the plunger 8 and syringe due to abutment between the rear tags 7A' with the plunger flange 8A and the front tags 7B' with the finger flange 90 of the syringe. During this movement the plunger 8 does not move relative the syringe and so no medicament exits from syringe.

The inner housing 7' continues to move the syringe and plunger 8 axially forward until the front tags 7B' are once again in radial alignment with the ribs 30c' of the outer housing 30'. The front tags 7B' then flex radially outwards into their original positions within the apertures 506 of the rear cylinder 500. At this point the syringe ceases to move axially forward as there is no longer a force being applied by the advancing inner housing 7' on the finger flange 90.

Since the syringe is stationary at this point, further advancement of the inner housing 7' causes the plunger 8 to move axially forward with respect to the syringe due to the abutment between the rear tags 7A' and the plunger flange 8A. As the plunger advances forward, medicament is expelled out of the syringe through the needle into the injection site.

Figure 21:
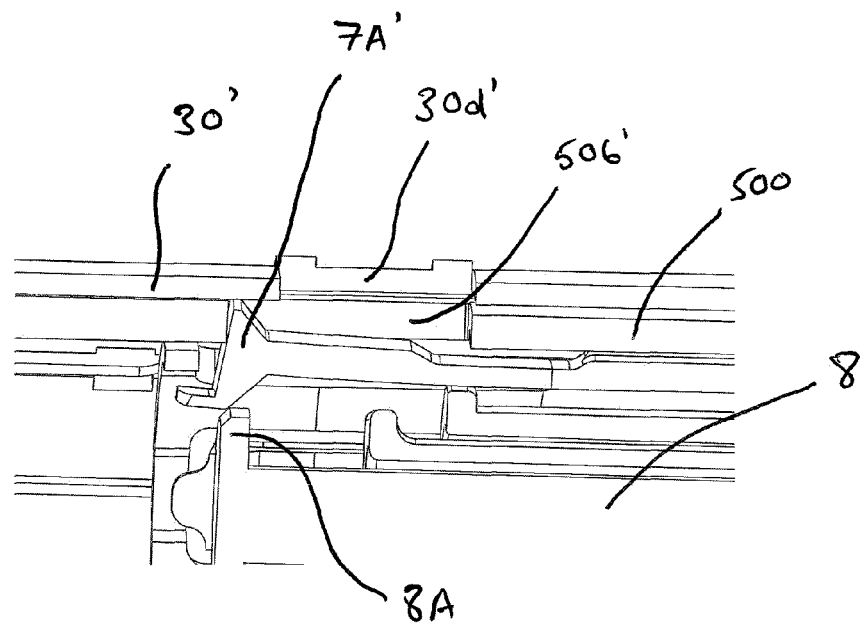
FIG. 21 is a partial cross sectional side view of the device of FIG. 15 after the plunger has advanced to its forwardmost axial position.

The advancing inner housing 7' continues to move the plunger 8A axially forward until the rear tags 7A' (which are radially flexible tags) reach a position (FIG. 21) where they are radially aligned with apertures 506' in the rear cylinder 500. When the rear tags 7A' reach this position, preferably all of the medicament (or at least the desired dose) has been expelled from the syringe.

It should be noted that since rear tags 7A' are orthogonal to front tags 7B' apertures 506' and 506 are also orthogonal with respect to the axial length of the rear cylinder 500.

When the rear tags 7A' are in radial alignment with the apertures 506', they flex partially radially outwards but are prevented from flexing radially outwards fully by abutment with the outer housing 30'. As a consequence the rear tags 7A' remain in the axial path of the plunger flange 8A (and act as a blocker in the form of a releasable latch) so that the plunger 8 and syringe are prevented from moving axially rearward under the bias of the return spring which acts as a biaser. Rearward movement of the syringe is required to retract the needle from the injection site. Retraction cannot take place therefore until the plunger 8 and syringe have a clear axial path within the device.

Figure 22:
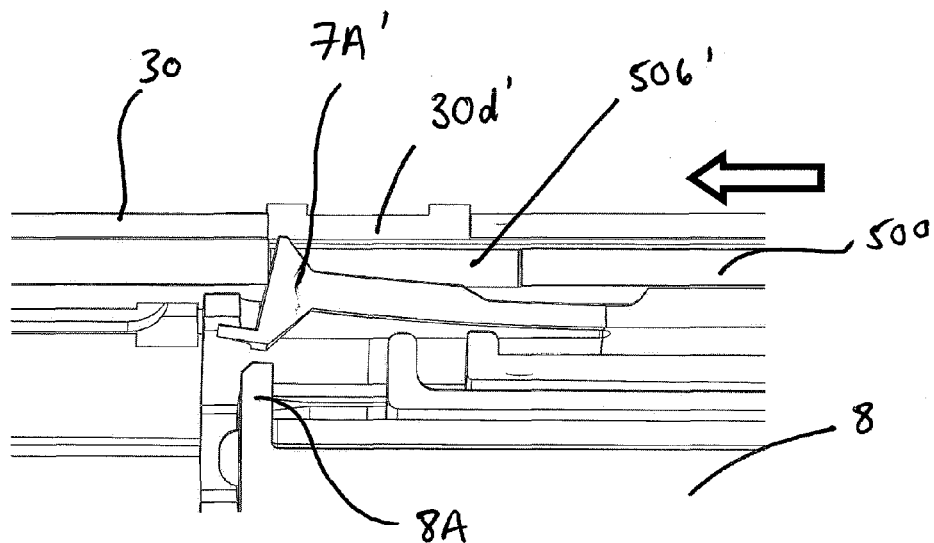
FIG. 22 is a partial cross sectional side view of the device of FIG. 15 as the outer housing is moved rearwardly with respect to the inner housing after a dose of medicament has been delivered.

Throughout the delivery of the medicament, the user will have maintained the forward axial force applied to the outer housing 30' thus compressing spring beam 504. Once delivery of the medicament is complete and the user has held the needle within the injection site for the desired dwell time, the user reduces the force on the outer housing 30'. When the forward force applied to the outer housing 30' is less than the biasing force of the compressed spring beam 504, the spring beam 504 decompresses causing the outer housing 30' to move rearward with respect to the rear cylinder 500 (as indicated by an arrow in FIG. 22). Consequently apertures 30d' in the outer housing 30' move into radial alignment with the apertures 506' in the rear cylinder 500 and the rear tags 7A'. The rear tags 7A' are then free to flex radially outwards into the apertures 30d' of the outer housing 30' and out of the axial path of the plunger 8 and syringe as shown in FIG. 22. The syringe, and hence needle, are then free to retract under the biasing influence of the return spring.

It will be appreciated that the present embodiment prevents needle retraction from occurring automatically immediately after medicament has been delivered. Instead, the present embodiment allows the user to determine the needle dwell time and initiates needle retraction by at least partially relieving the pressure on the outer housing 30'. As with the first embodiment comprising a retraction ring described above, the user need not necessarily remove the device from the injection site to activate needle retraction. It is therefore possible to administer medicament and withdraw the needle into the housing of the device without the needle ever being visible to the user. Such a feature is advantageous for patients with a phobia of needles and can prevent needle stick injury before and after use.

In a third embodiment of the invention, the user once again is able to initiate retraction by relieving the forward force applied to the outer housing. However, retraction is initiated internally by different mechanical means than those described above.

Figure 23A:
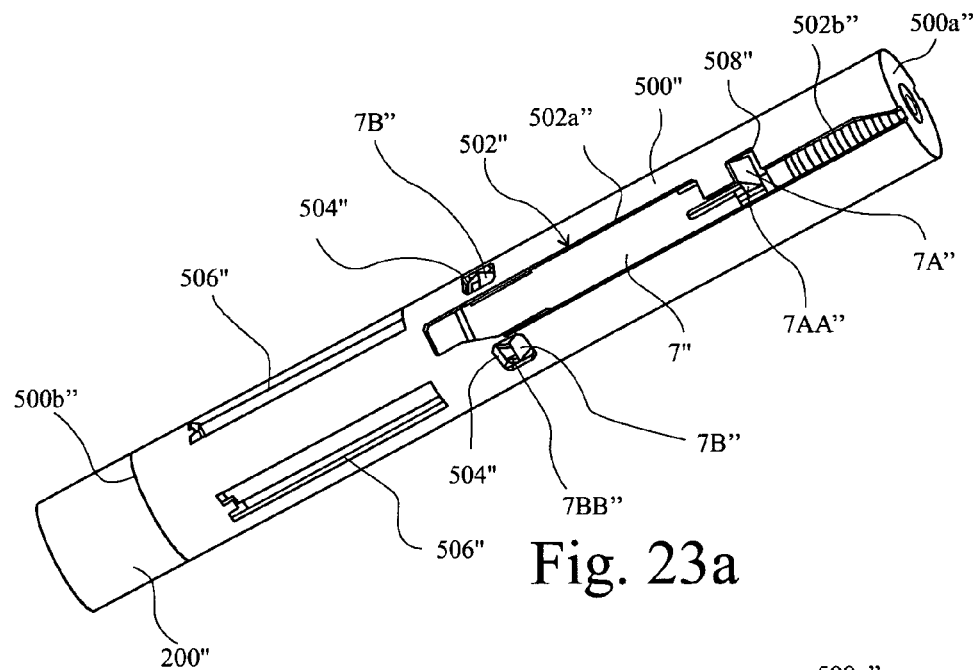
FIG. 23a is a perspective view of a device having a modified rear cylinder and inner housing (outer housing not shown for clarity)

In the device shown in FIG. 23 a modified rear cylinder 500" (or "rear housing") has two identical longitudinally extending rear slots 502" (only one slot 502" is shown). A modified outer housing 30" is normally disposed around the outside of rear cylinder 500" but is not shown in FIG. 23a for clarity. The rear slots 502" are equally spaced around the circumference of the rear cylinder 500". Four apertures forming windows 504" are situated intermediate a rear end 500a" and a front end 500b" of the rear cylinder 500". Four corresponding front slots 506" are disposed intermediate the front end 500b" of the rear cylinder 500" and the four windows 504" and are in axial alignment with, but not connected to, the windows 504". A front housing 200" is attached to the forwardmost end 500b" of the rear cylinder 500".

Each rear slot 502" extends from the rear end 500a" of the rear cylinder 500" and has a wide portion 502a" that is forward of a narrow portion 502b" wherein the angular extent of the narrow portion 502b" is less than that of the wide portion 502a" across the rear cylinder's 500" circumference. In the narrow portion 502b" a recess 508" is formed that extends circumferentially from the slot 502".

Disposed within the rear cylinder 500" is a modified inner housing 7" having two radially flexible rear legs 7A" and four radially flexible front legs 7B". The two rear legs 7A" and four front legs 7B" are spaced equally around the circumference of the inner housing 7" respectively. Each leg 7A", 7B" is generally L-shaped with a longitudinally extending flexible portion and a radially extending head such that the legs 7A", 7B" are capable of flexing in a radial direction. Prior to use, as shown in FIG. 23, the heads of the front legs 7B" are disposed within the windows 504" of the outer housing 500". Similarly the head of the rear leg 7A" is disposed within the recess 508". In this position, the inner housing 7" cannot move relative the rear cylinder 500". As shown more clearly in FIG. 26, front legs 7B" have a ramped surface where the forward most ramp has a cut out 7BB".

Other embodiments of the invention are envisaged where the inner housing 7" has a different number of legs 7A", 7B" and the outer housing 500" has a different number of windows 504" and recesses 508".

Figure 23B:
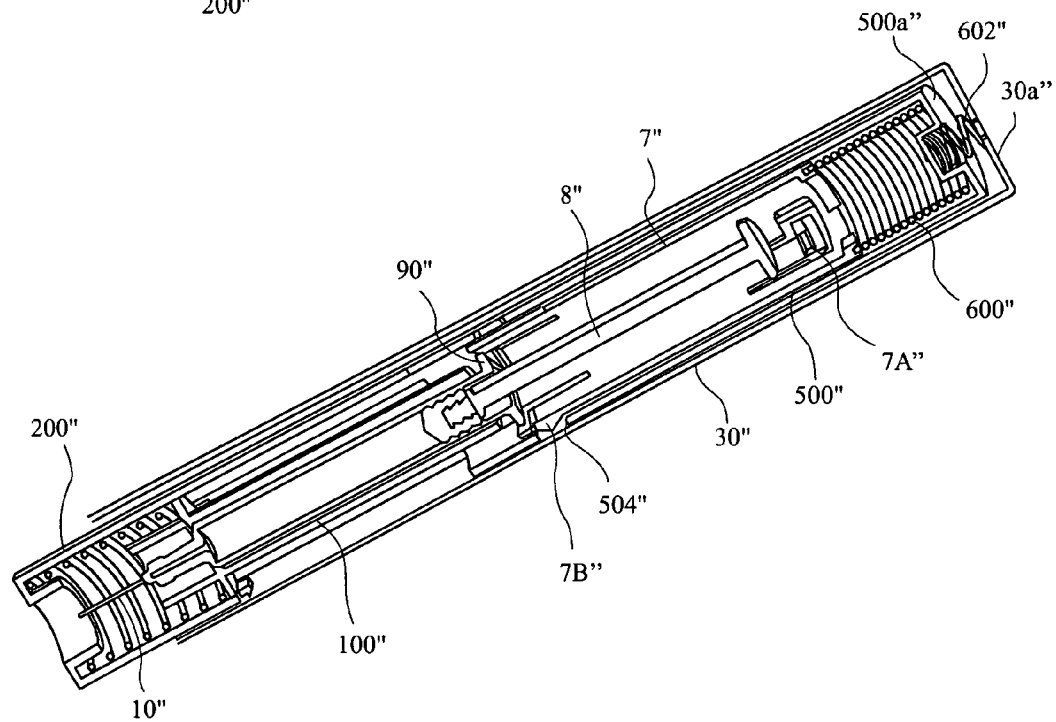
Figure 23C:
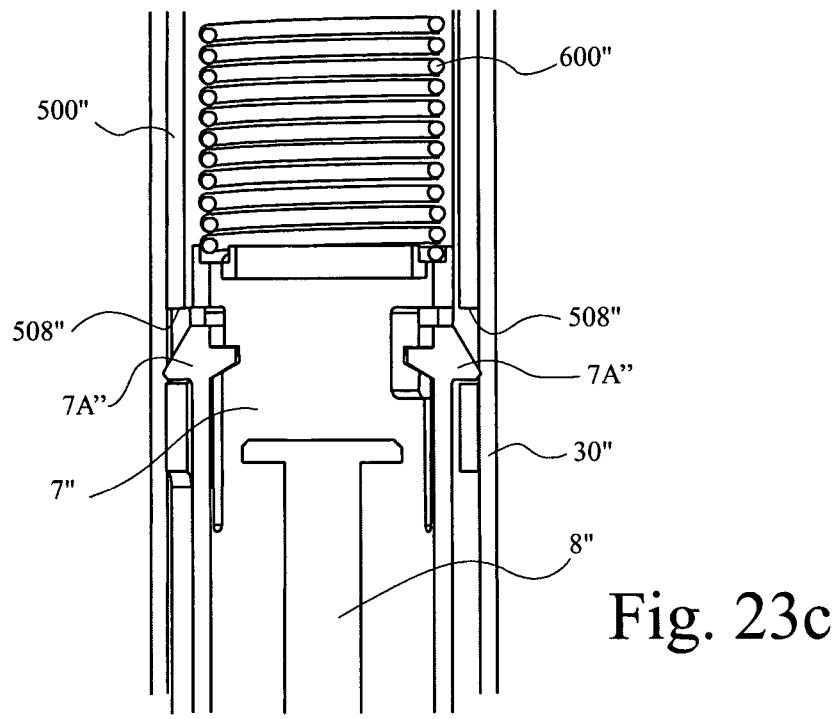

FIG. 23b shows a cross section of the device (complete with modified outer housing 30") of FIG. 23a where it can be seen that within the rear cylinder 500", a syringe having a needle 10" is held in a syringe holder 100". The syringe has a finger flange 90" that is disposed forward of the front legs 7B" prior to use. A plunger is located within the syringe and is in an non-depressed state prior to use (as shown in FIG. 23b), extending rearwardly, terminating forward of the rear legs 7A". The inner housing 7" is biased forwardly by a compressed drive spring 600" that is attached to the rear end 500a" of the rear cylinder 500". Since the heads of legs 7A" are located in recesses 508", the inner housing 7" cannot travel forward under the influence of drive spring 600". FIG. 23c shows a detailed view of the legs 7A" located in recesses 508".

A secondary return spring 602" connects the rear end 500a" of the rear cylinder 500" and a rear end 30a" of the outer housing 30". It will be apparent to the skilled reader that any suitable biasing member, such as a spring beam, may be used in place of secondary return spring 602". Prior to use, in the state shown in FIG. 23b, the secondary return spring 602" is relaxed and does not bias the outer housing 30" or rear cylinder 500" in any direction.

Figure 24:
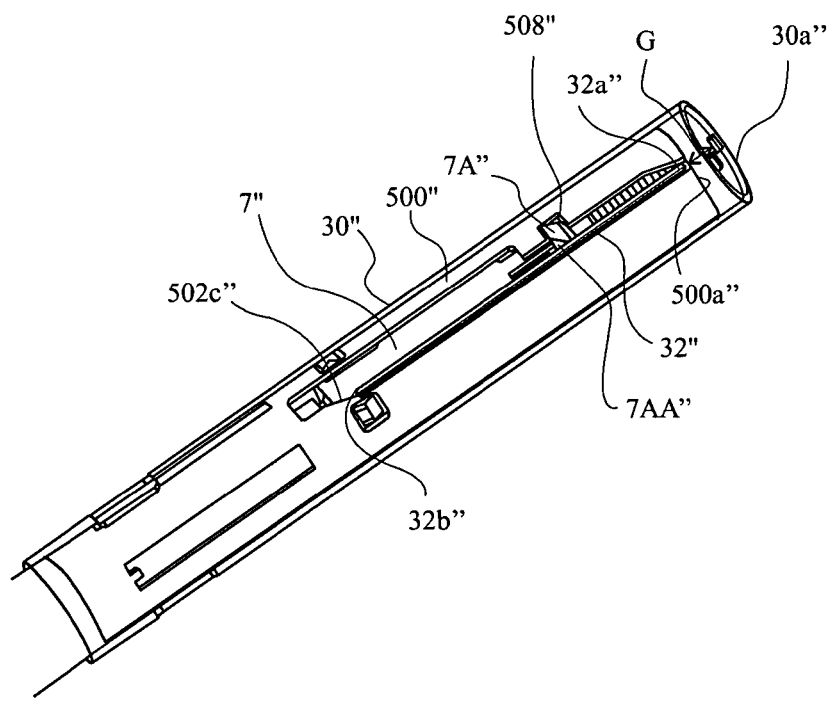
FIG. 24 is a perspective view of the device of FIG. 23a showing the modified outer housing prior to actuation.

FIG. 24 shows the device complete with modified outer housing 30". The outer housing 30" is shown as transparent in FIG. 24 to aid understanding. The modified outer housing 30" comprises two longitudinally extending ribs 32" on its inner surface that are equally spaced around its inner circumference. One such rib 32" is visible in FIG. 24. The ribs 32" extend radially inwards from the inner surface of the outer housing 30". As can be seen, the ribs extend along a rear portion of the outer housing 30" but terminate before reaching a rear end 30a" of the outer housing 30". A gap G is therefore left between the rear end 32a" of the rib 32" and the inner surface of the rear end 30a" of the outer housing 30". Prior to use, as shown in FIG. 24, the gap G is approximately equal to the distance between the rear end of the rear cylinder 500a" and the inner surface of the rear end of the outer housing 30a".

Prior to actuation of the device, in the position shown in FIG. 24, the ribs 32" are disposed in the slots 502" such that they do not impinge on the heads of rear legs 7A". The ribs 32" may be in contact with a ramped surface 7AA" of the rear legs 7A" although the rear legs will remain in an unflexed position, with their heads protruding through recesses 508".

Figure 25A:
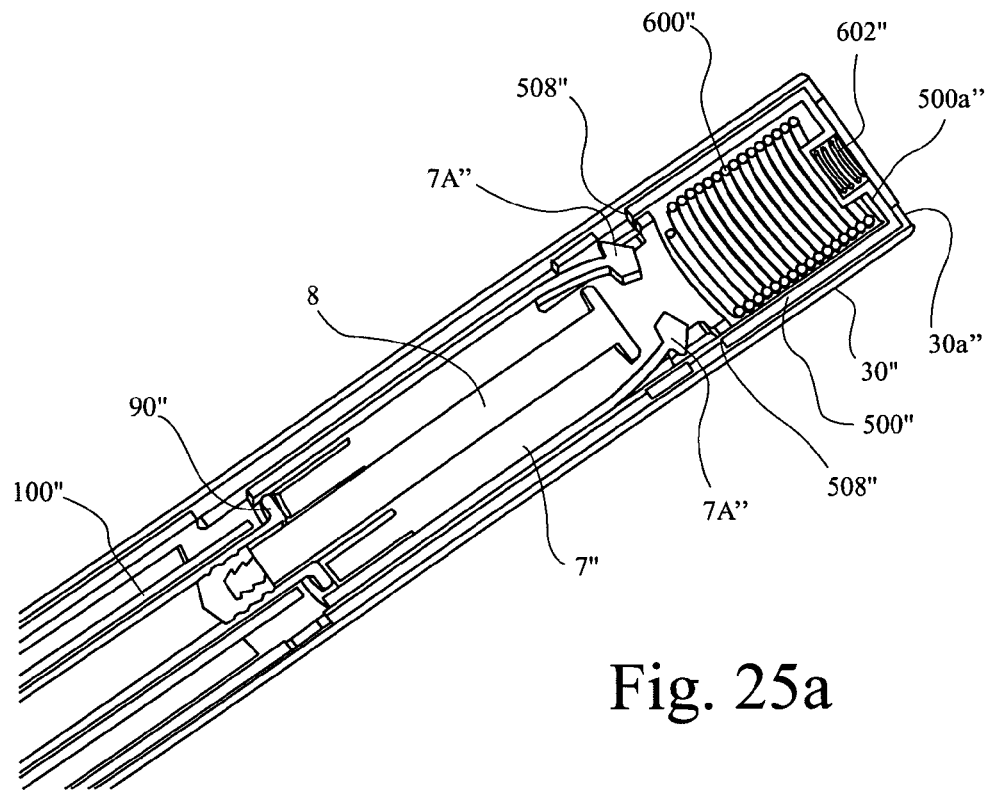
FIG. 25a is a cross sectional view of the device of FIG. 23a after the outer housing has been moved forwardly and circumferentially with respect to the rear cylinder and FIG. 25b is a corresponding partial perspective view showing the rear legs flexed radially inwards.
Figure 25B:
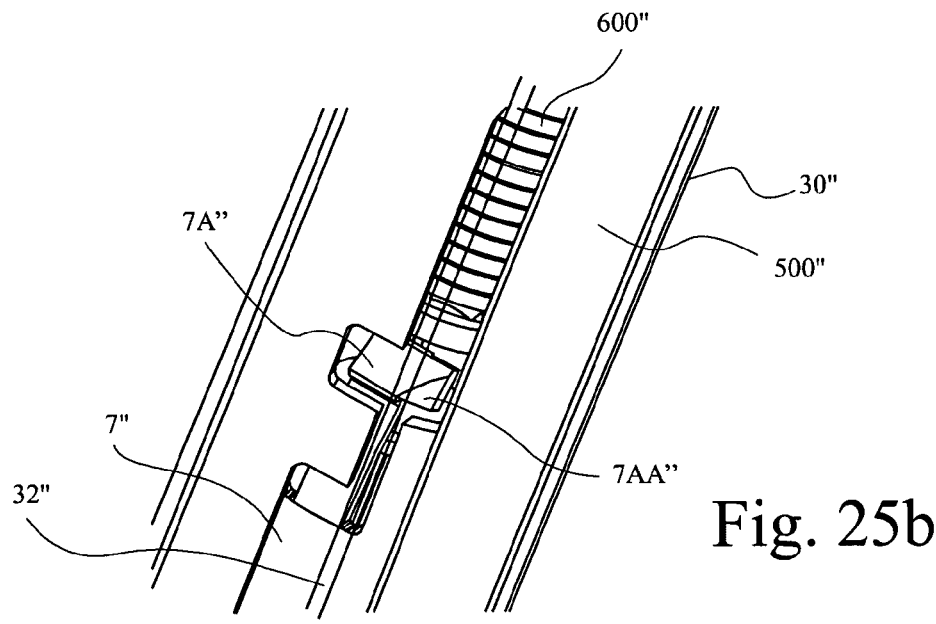

When the user is ready to actuate the device and deliver an injection, he places the forward end of the device against the patient's skin at the desired injection site and pushes the outer housing 30" forward towards the injection site. As the outer housing 30" moves forward relative to the rear cylinder 500", the secondary return spring 602" is compressed and forward ends 32b" of ribs 32" come into contact with first ramps 502c" of the slots 502". The contact between the ribs 32" and ramps 502c" causes the outer housing 30" to rotate with respect to the rear cylinder 500". As the outer housing rotates 30", ribs 32" move across the ramped surfaces 7AA" of rear legs 7A". The contact between the ribs 32" and flexible rear legs 7A" causes the rear legs 7A" to flex radially inwards such that their heads no longer protrude through recesses 508" (see FIGS. 25a and 25b).

Figure 26:
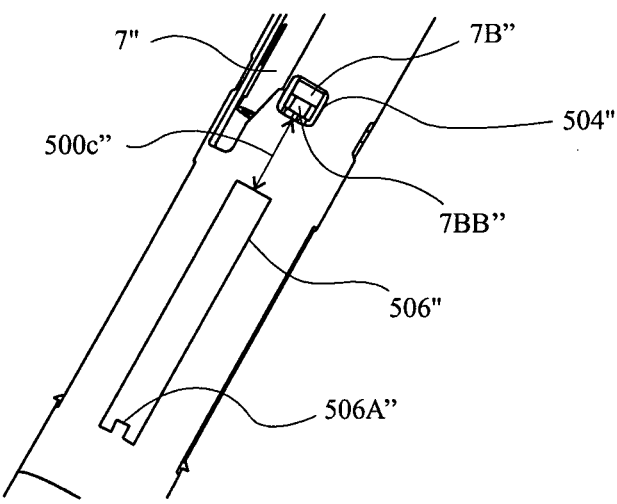
FIG. 26 is a partial perspective view of the device of FIG. 23a showing the front legs of the inner housing and intermediate section and a front slot of the rear cylinder.

With rear legs 7A" flexed radially inwards, the inner housing 7" is no longer restrained with respect to the rear cylinder 500" and the force of drive spring 600" acting as an energy source causes the inner housing 7" to advance forwards within the rear cylinder 500". The forwardly advancing inner housing 7" causes front legs 7B" to flex radially inwards through contact between the ramped surfaces of front legs 7B" and the edges of windows 504". FIG. 26 shows the front legs 7B" in windows 504" just prior to flexing radially inwards and moving forwards.

Figure 27:
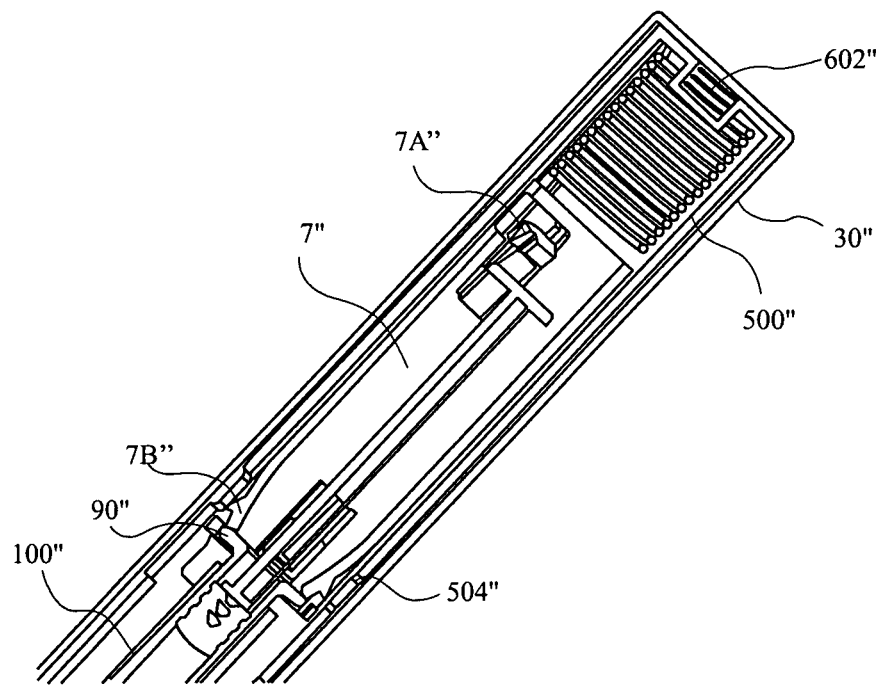
FIG. 27 is a cross sectional view of the device of FIG. 23a showing the front legs in communication with the barrel of the syringe and the rear legs flexed radially inwards.

FIG. 27 shows the front 7B" and rear 7A" legs flexed radially inwards shortly after the inner housing 7" has started to advance forwards. The front legs 7B" are in axial alignment with the syringe barrel 90" and so the advancing inner housing 7" causes the syringe holder 100" to advance forwards also and expose the needle 10" from the front end of the device.

Figure 28A:
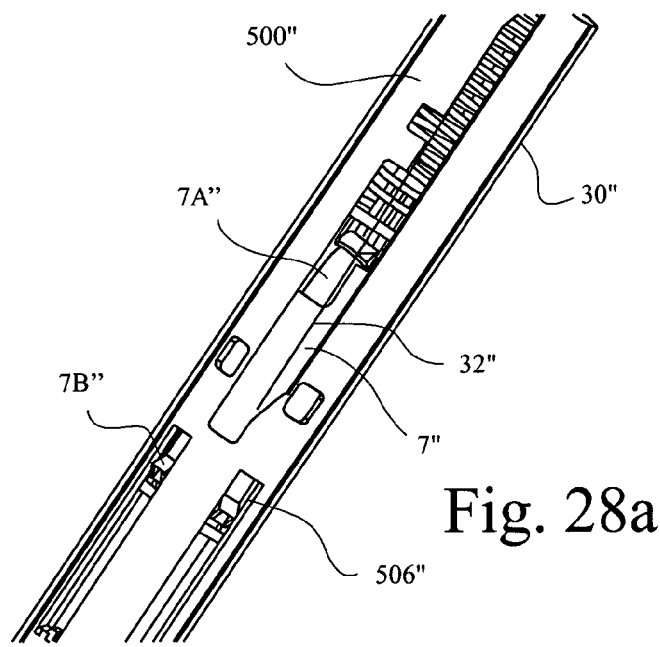
FIG. 28a is a partial perspective view of the device of FIG. 23a during delivery showing the front legs disposed in the front slots of the rear cylinder and FIG. 28b is a corresponding cross sectional view showing the rear legs in communication with the plunger.
Figure 28B:
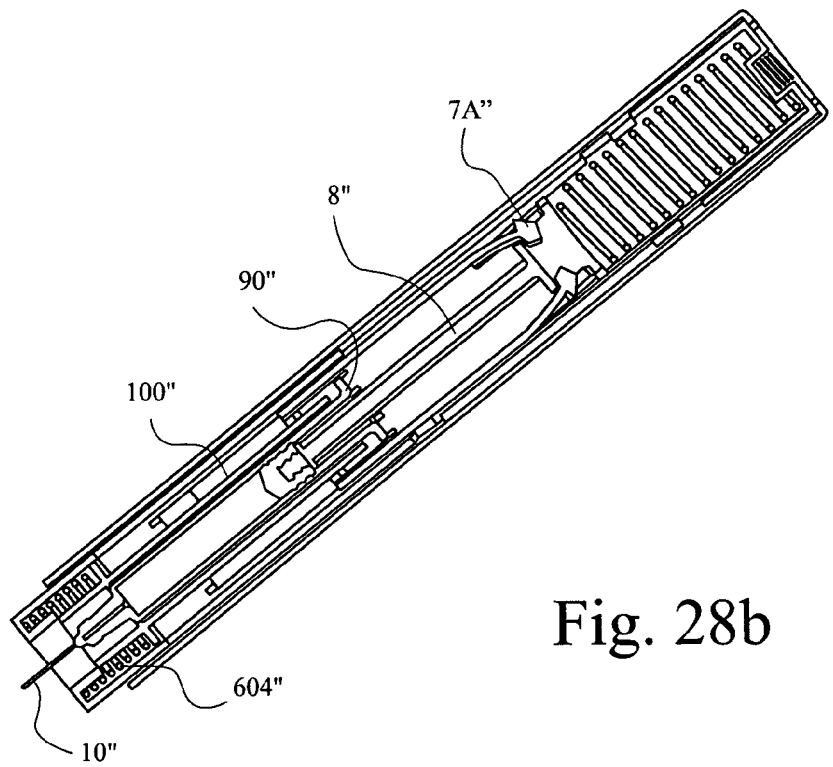

As the inner housing 7" advances forwards within rear cylinder 500", front legs 7B" are only in axial alignment with the syringe barrel as long as they are in radial alignment with intermediate section 500c" of the rear cylinder 500" (see FIG. 26). As soon as front legs 7B" are forward the intermediate section 500c", the front legs come into axial alignment with front slots 506" and flex radially outwards once more and out of axial alignment with the syringe barrel. After this point, the inner housing will continue to advance forwards with the heads of the front legs 7B" disposed within front slots 506". FIGS. 28a and 28b show the device when the front legs 7B" have flexed radially outwards into front slots 506".

As the inner housing 7" continues to advance forwards, the rear legs 7A" remain flexed radially inwards due to the position of ribs 32". As FIG. 28b shows, the forward moving rear legs 7A" then come into contact with the plunger 8" of the syringe and depress it within the syringe expelling the medicament contained within. At this point, the front legs have flexed radially outwards into front slots 506" and so no longer act upon the finger flange 90". The needle is therefore exposed and in its most forwardly position and does not continue to advance forwards. A primary return spring 604", located between the syringe holder 100" and the injection site is in a compressed state at this stage.

However, the inner housing 7" does continue to advance forwards within the rear cylinder 500" (all the while expelling medicament) until front legs 7B" encounter stops 506A" that are formed on a forwardmost end of front slots 506". The stops 506A" comprise tabs that extend axially rearwards from the front end of front slots 506". When the front legs 7B" come into contact with the stops 506A", the stops 506A" engage with cut outs 7BB" of front legs 7B" and prevent their ramped surfaces reaching the front end of front slots 506" thus preventing them from flexing radially inwards once again. When the stops 506A" engage the front legs 7B", therefore, they arrest the forward movement of the inner housing 7" with respect to the rear cylinder 500". It is preferable that the plunger has traveled its full length within the syringe barrel at this point and the entire dose of medicament has been delivered. In alternative embodiments, however, it may be preferable for a partial dose to have been delivered at this point.

When the dose of medicament has been delivered, the next stage of the process is the retraction of the needle from the injection site. For the reasons discussed above, however, in some cases, it is desirable for the user to decide when retraction should take place, thus determining the dwell time of the needle. In the present embodiment, after the medicament has been delivered (either entirely or partially), the syringe is prevented from retracting back into the device under the influence of the primary return spring 604" due to the rear legs 7A" (which form radially flexible tags) of the inner housing 7" (acting as a blocker in the form of a releasable latch) blocking the retraction path. More specifically, the inner housing 7A" is held in a forward position under the influence of the main drive spring 600" and the rear legs 7A" are held radially inwards due to contact with ribs 32" so the force of the drive spring 600" is exerted on the plunger 8" and syringe also. Since the force exerted by the drive spring 600" is greater than that of the primary return spring 604", the syringe is prevented from retracting.

For the syringe to retract, the user must reduce the forward force on the outer housing 30" so that it can move rearward with respect to the rear cylinder 500" under the influence of the secondary return spring 602" that is connected therebetween.

FIGS. 29-32 relate to the retraction of the needle following partial delivery of a medicament dose. In this situation, the user wishes to terminate the injection before the entire dose has been delivered. In prior art devices, withdrawing the needle before the entire dose has been delivered will lead to the medicament continuing to be expelled which may be hazardous, or at least inconvenient and undesirable. The present invention provides means for withdrawing the needle mid-delivery without the above-mentioned disadvantages.

As soon as the user relieves the forward force on the outer housing 30", the secondary return spring 602" acts to draw the outer housing 30" rearwards with respect to the rear cylinder 500". As this happens, the rear ends 32a" of ribs 32" come into contact with a ramped surface 502d" (see FIG. 29) at the rear of slot 502" causing the outer housing 30" to rotate with respect to the rear cylinder 500". The outer housing 30" rotates until the ribs 32" reach the rear most part of slots 502" and the ribs 32" are disposed in their original positions (prior to actuation) within slots 502". This position is shown in FIG. 29 where it can be seen that the relative positions of the outer housing 30" and rear cylinder 500" are the same as they were prior to actuation (see FIG. 24, for example).

Figure 29:
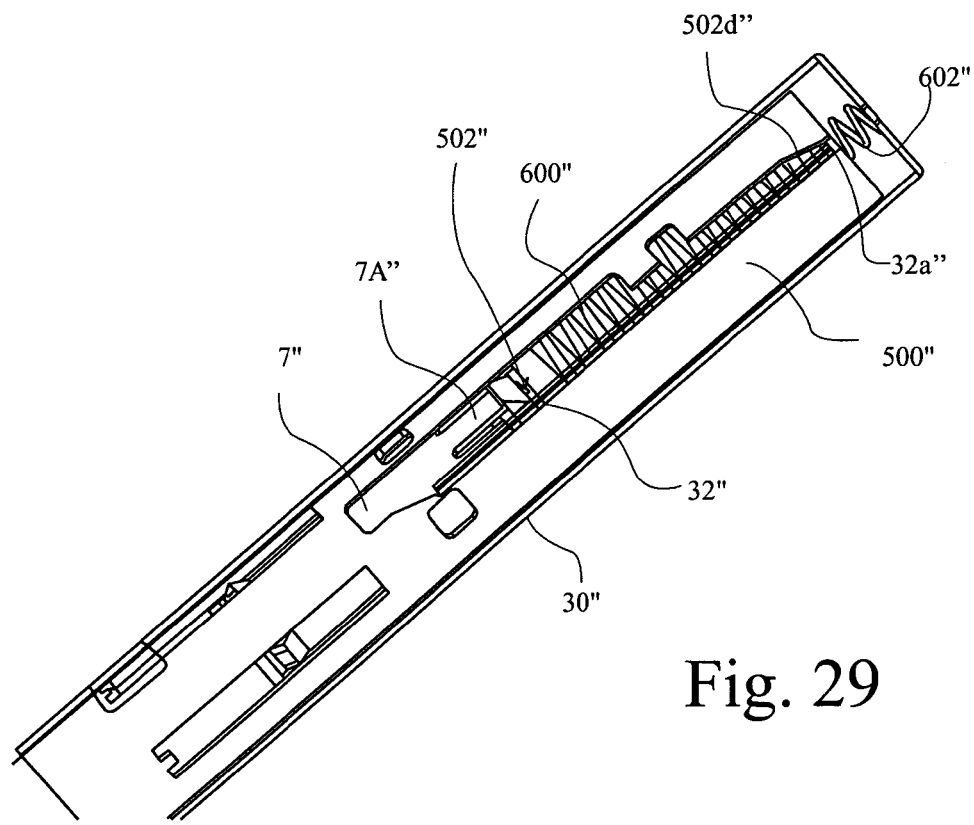
FIG. 29 is a perspective view of device of FIG. 23a after the user has initiated retraction following the partial delivery of a dose of medicament.
Figure 30:
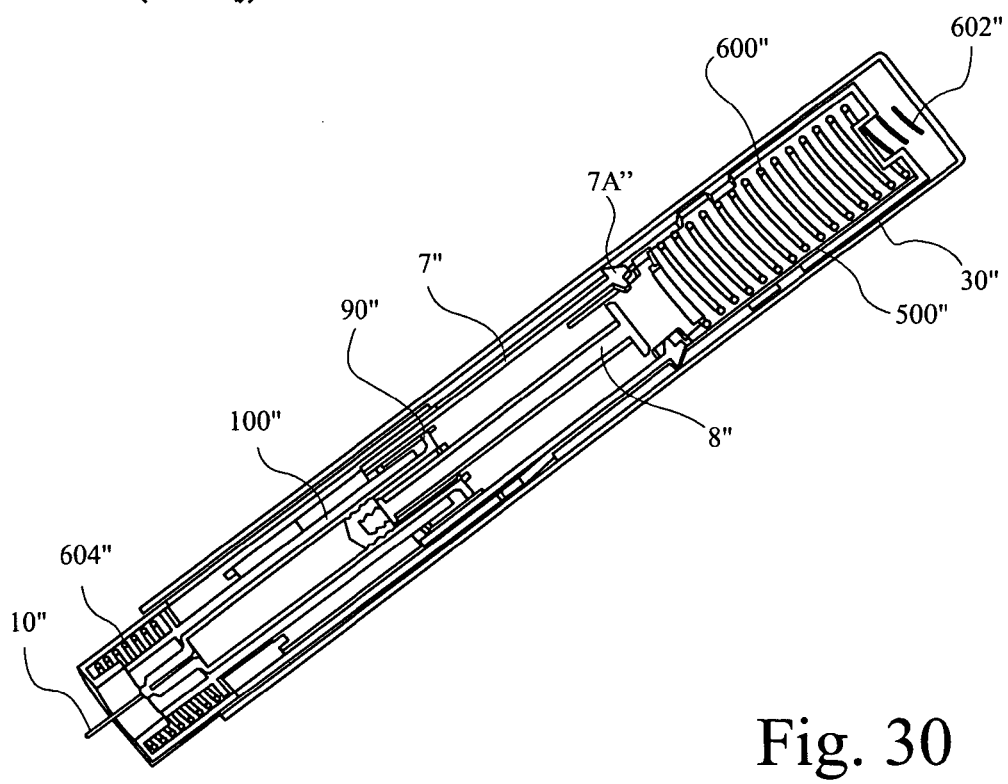
FIG. 30 is a cross sectional view of the device of FIG. 23a showing the rear legs flexed radially outwards, out of the retraction path of the syringe assembly, following the partial delivery of a dose of medicament.
Figure 31:
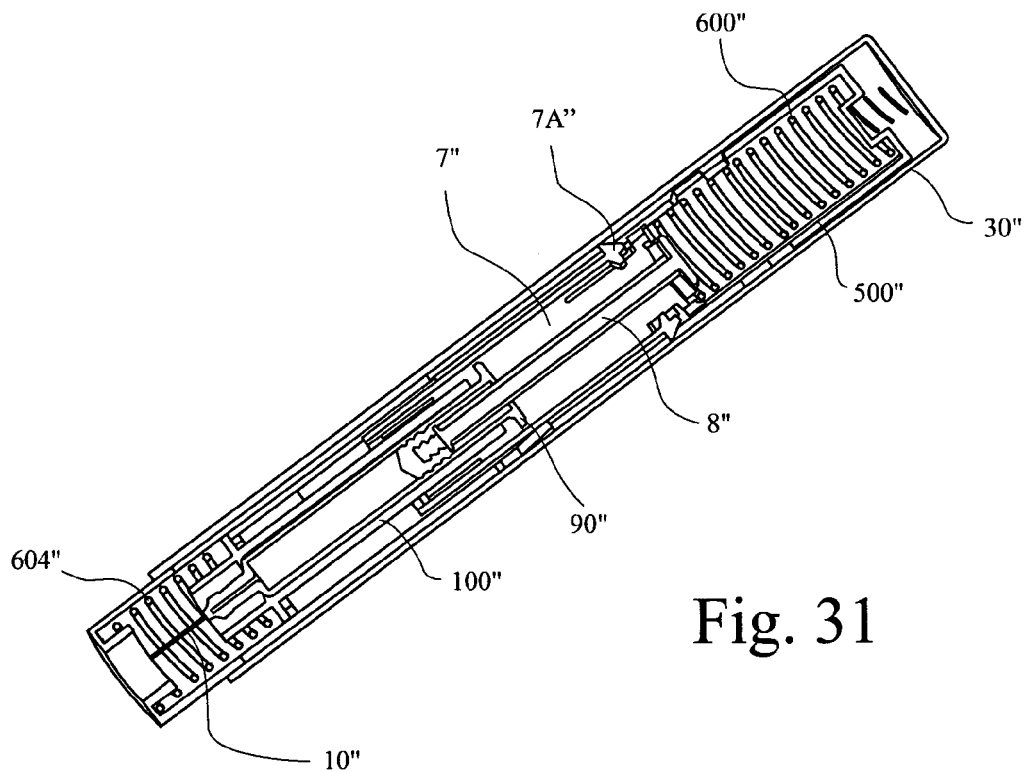
FIG. 31 is a cross sectional view of the device of FIG. 23a showing the syringe assembly in a retracted position but where the inner housing has not traveled to its forwardmost position, following the partial delivery of a dose of medicament.
Figure 32:
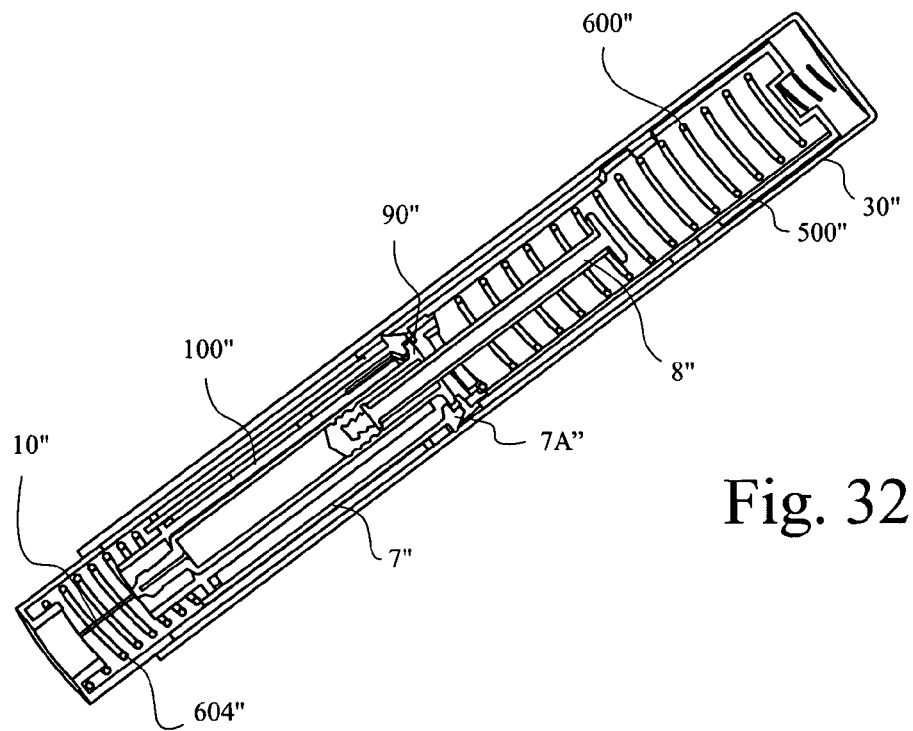
FIG. 32 is a cross sectional view of the device of FIG. 23a showing the syringe assembly in a retracted position and the inner housing in its forwardmost position, following the partial delivery of a dose of medicament.

When the ribs 32" rotate to the position shown in FIG. 29, they move out of contact with the heads of rear legs 7A", allowing them to flex radially outwards one more into slots 502". As FIG. 30 shows, the unflexed rear legs 7A" provide a clear axial path for the syringe and plunger assembly to move rearwards under the influence of the primary return spring 604" which acts as a biaser. Consequently, the plunger is no longer pushed forwards within the syringe, so no more medicament is expelled and the needle 10" is withdrawn from the injection site (FIG. 31). Meanwhile, the inner housing 7" continues to move forwards under the influence of the drive spring 600". Because all front 7B" and rear 7A" legs are unflexed at this point, the inner housing 7" does not interfere with the syringe assembly and so does not affect the retraction thereof. The inner housing 7" continues its forward advancement until cut outs 7BB" of front legs 7B" reach the stops 506A" as described above. FIG. 32 shows the device in its final position after retraction has taken place following a partial delivery of medicament. In FIG. 32, it is clear that only a portion of the medicament has been delivered since the plunger 8" has not traveled the entire length within the syringe.

Figure 33:
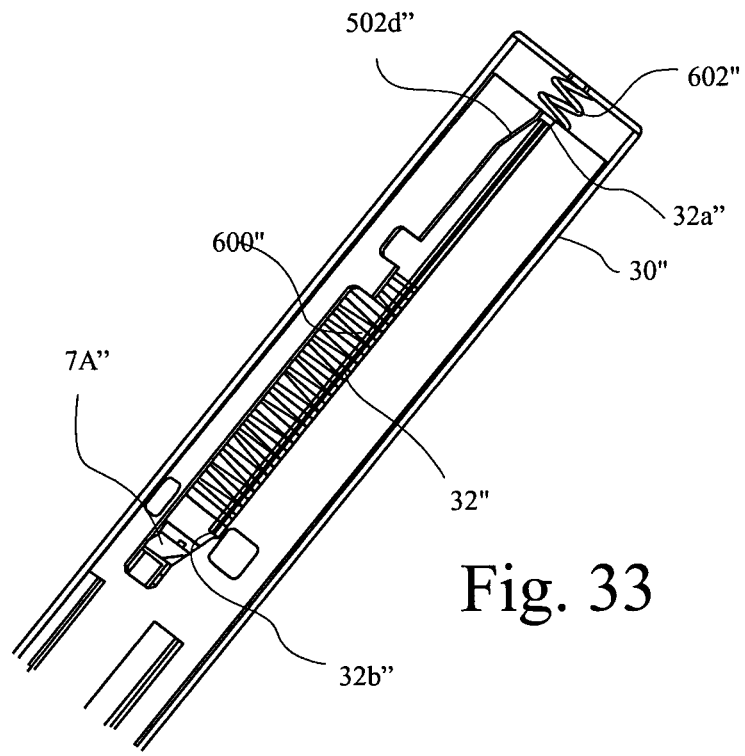
FIG. 33 is a partial perspective view of the device of FIG. 23a after the user has initiated retraction following the delivery of the entire contents of the syringe.
Figure 34:
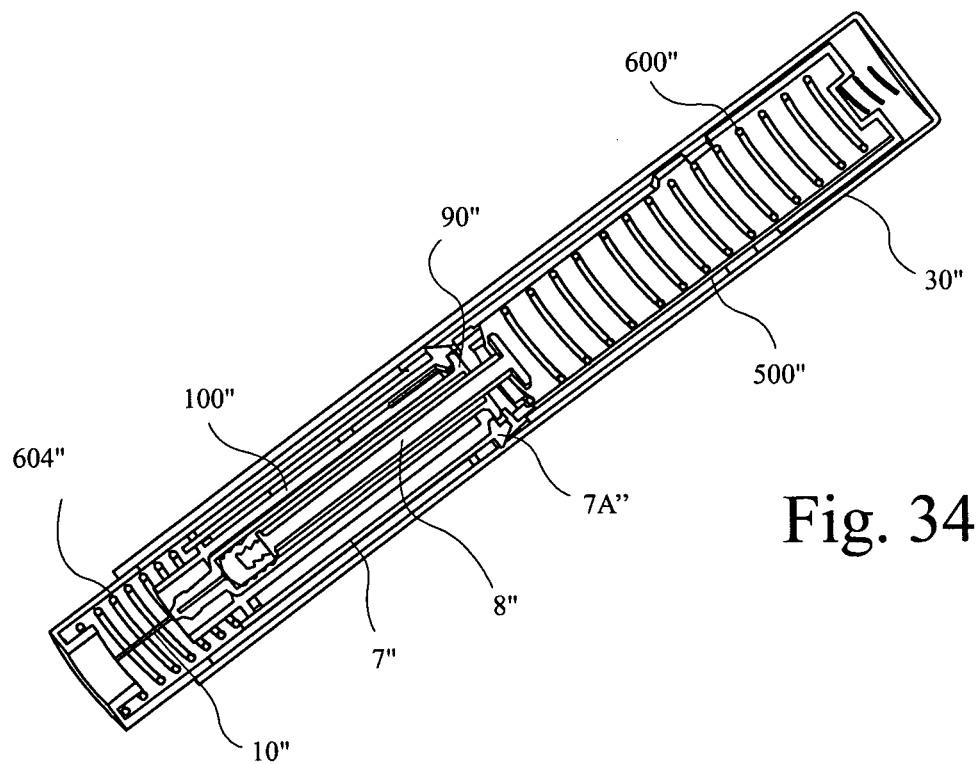
FIG. 34 is a cross sectional view of the device of FIG. 23a showing the syringe assembly in a retracted position and the inner housing in its forwardmost position, following the delivery of the entire contents of the syringe.

In the case that delivery is allowed to continue until all medicament has been delivered, the rear legs 7A" will have traveled to be in radial alignment with the forward ends 32b" of ribs 32". Again retraction is initiated by relieving the forward force on the outer housing 30" and allowing the rear end 32a" of the ribs to move along ramped sections 502d" of slots 502" and rotate the outer housing 30" relative the rear cylinder 500'. This position is shown in FIG. 33 where it can be seen that the rear legs 7A" have traveled further forwards than in FIG. 29, where only partial delivery had taken place. FIG. 34 shows a cross section of the device after retraction has taken place following the delivery of a full dose of medicament. In contrast to FIG. 32, the plunger has traveled the entire length within the syringe and expelled all of the medicament contained therein.

In another embodiment (not illustrated) it would be possible to configure the device such that automatic retraction occurs when the full dose of medicament has been delivered, but where the controlled automatic retraction can still be actuated by the user part way through delivery, if so desired. One particular way of achieving this may be to shorten the length of ribs 32" such that at the point where the plunger has reached its forwardmost position within the syringe, the rear legs 7A" are forward of the frontmost ends 32b" of ribs 32" and flex radially outwards.

It is also envisaged that retraction of the needle could be actuated either selectively by the user, or automatically in the event of any fault with the autoinjector which might put the user at risk of injury from an exposed needle.

The disclosure set forth above encompasses multiple distinct inventions with independent utility. While each of these inventions has been disclosed in a preferred form or method, the specific alternatives, embodiments, and/or methods thereof as disclosed herein are not to be considered in a limiting sense, as numerous variations are possible. The present disclosure includes all novel and non-obvious combinations and subcombinations of the various elements, features, functions, properties, methods and/or steps disclosed herein. Similarly, where any disclosure above recites "a" or "a first" element, step of a method, or the equivalent thereof, such disclosure should be understood to include one or more such elements or steps, neither requiring nor excluding two or more such elements or steps.

Inventions embodied in various combinations and subcombinations of features, functions, elements, properties, steps and/or methods may be recited in claims of a related application. Such claims, whether they focus on a different invention or the same invention, and whether different, broader, narrower, or equal in scope to the original claims, are also regarded as included within the subject matter of the present disclosure.

The invention claimed is:

1. An autoinjector, including
   a housing, in which can be mounted a syringe having a plunger, a barrel and needle at one end thereof through which medicament can be delivered to an injection site;
   a syringe support capable of causing said syringe to move therewith along an axial path with respect to said housing;
   a biaser capable of biasing said syringe support so that said needle is normally inside said housing; and
   a blocker that includes a releasable latch, wherein the blocker is constructed to be selectively moveable by a user to a first position by application of a forward force such that the blocker substantially prevents rearward movement of the syringe along said axial path, and from the first position to a second position by reduction of the forward force whereby the blocker allows rearward movement of the syringe along said axial path relative to said housing and wherein said biaser causes said needle to retract inside said housing.

2. The autoinjector of claim 1 wherein said housing includes
   an outer housing;
   an inner housing, at least part of which is positionable, in use, intermediate the outer housing and the syringe support; and
   a rear housing intermediate said outer housing and said inner housing,
   the autoinjector further comprising an energy source in communication with said inner housing, the inner housing being moveable by the energy source between three positions, namely
   a first position of the inner housing in which the inner housing is in communication with the barrel such that, in use, the plunger and barrel are movable axially so as to move at least part of said needle out of the outer housing;
   a second position of the inner housing in which the inner housing is in communication with the plunger but not the barrel such that, in use, said plunger is movable axially into said barrel so as to expel medicament through the needle; and
   a third position of the inner housing in which the inner housing is in communication with neither the plunger nor the barrel such that, in use, the plunger and barrel are able to retract in order to retract the needle into the outer housing.

3. The autoinjector of claim 2 wherein said blocker comprises a releasable latch between said housing and said syringe support means.

4. The autoinjector of claim 3 wherein said biaser comprises a needle return spring at a forward end of said autoinjector, and said locking ring being forward biased by said needle return spring.

5. The autoinjector of claim 4 wherein said releasable latch is located at a front end of said syringe support.

6. The autoinjector of claim 3 wherein said releasable latch is located at a front end of said syringe support.

7. The autoinjector of claim 2 wherein said blocker comprises a releasable latch between at least part of an inner housing and a rear housing.

8. The autoinjector of claim 7 further comprising rearward biaser between said outer housing and said rear housing.

9. The autoinjector of claim 2 wherein said blocker comprises a releasable latch between at least part of said outer housing and said rear housing.

10. The autoinjector of claim 9 wherein said releasable latch comprises a longitudinal slot in one of said outer housing and rear housing, into which a rib or protrusion on the other of said outer housing and rear housing can engage.

11. The autoinjector of claim 10 wherein said longitudinal slot has a main section of substantially constant width and a forwardmost section of narrowed width with a tapered edge therebetween, wherein, in use, forward movement of said rib or protrusion in said slot is guided by said tapered edge so as to cause rotary movement of said rib or protrusion about the longitudinal axis of the autoinjector.

12. The autoinjector of claim 11 wherein said longitudinal slot is in said rear housing and said a rib or protrusion is on the interior surface of said outer housing.

13. The autoinjector of claim 10 wherein said longitudinal slot is in said rear housing and said a rib or protrusion is on the interior surface of said outer housing.

14. The autoinjector of claim 1 wherein said blocker is selectively moveable by a user from said first position to said second position by the reduction of a previously-applied forward force after delivery of a partial, but not necessarily complete, dose of medicament.

15. The autoinjector of claim 14 wherein said blocker comprises a releasable latch between said housing and said syringe support means.

16. The autoinjector of claim 15 wherein said releasable latch is located at a front end of said syringe support.

17. The autoinjector of claim 14 wherein said blocker comprises a releasable latch between at least part of an inner housing and a rear housing.

18. The autoinjector of claim 17 further comprising rearward biaser between said outer housing and said rear housing.

19. The autoinjector of claim 14 wherein said blocker comprises a releasable latch between at least part of said outer housing and said rear housing.

20. The autoinjector of claim 19 wherein said releasable latch comprises a longitudinal in one of said outer housing and rear housing, into which a rib or protrusion on the other of said outer housing and rear housing can engage.

21. The autoinjector of claim 1 wherein said blocker comprises a releasable latch between said housing and said syringe support means.

22. The autoinjector of claim 21 wherein said releasable latch includes a forward biased locking ring.

23. The autoinjector of claim 22 wherein said releasable latch is located at a front end of said syringe support.

24. The autoinjector of claim 21 wherein said releasable latch is located at a front end of said syringe support.

25. The autoinjector of claim 1 wherein said blocker comprises a releasable latch between at least part of an inner housing and a rear housing.

26. The autoinjector of claim 25 wherein said releasable latch comprises a radially-flexible tag on said inner housing which is capable of moving into and out of engagement with an aperture or recess in said rear housing.

27. The autoinjector of claim 26 further comprising rearward biaser between said outer housing and said rear housing.

28. The autoinjector of claim 25 further comprising rearward biaser between said outer housing and said rear housing.

29. The autoinjector of claim 28 wherein said rearward biaser comprises a spring beam or a spring intermediate a rear end of said rear housing and said outer housing.

30. A method of delivering medicament using an autoinjector as claimed in any of the preceding claims comprising the steps of:
 placing the forward end of the autoinjector at an injection site;
 applying a forward force to the autoinjector which a) engages said blocker and releasable latch into said first position and b) initiates delivery of medicament; and
 reducing said forward force at a time selected by the user which a) causes said blocker and releasable latch to move into said second position and b) permits retraction of said needle into said housing.

* * * * *